United States Patent [19]
Harling et al.

[11] Patent Number: 6,110,934
[45] Date of Patent: Aug. 29, 2000

[54] SUBSTITUTED BENZAMIDE DERIVATIVES AND THEIR USE AS ANTICONVULSANTS

[75] Inventors: John David Harling, Sawbridgeworth; Barry Sidney Orlek, Epping; Mervyn Thompson, Harlow, all of United Kingdom

[73] Assignee: SmithKline Beecham p.l.c., Brentford, United Kingdom

[21] Appl. No.: 09/202,524

[22] PCT Filed: Jun. 13, 1997

[86] PCT No.: PCT/EP97/03131

§ 371 Date: Dec. 16, 1998

§ 102(e) Date: Dec. 16, 1998

[87] PCT Pub. No.: WO97/48683

PCT Pub. Date: Dec. 24, 1997

[30] Foreign Application Priority Data

Jun. 17, 1996 [GB] United Kingdom .................... 9612608
Jul. 22, 1996 [GB] United Kingdom .................... 9615352
May 28, 1997 [GB] United Kingdom .................... 9711013

[51] Int. Cl.$^7$ .................... C07D 217/04; A61K 31/47
[52] U.S. Cl. .................... 514/307; 546/146; 514/213.01; 514/412; 540/593; 548/503
[58] Field of Search .................... 546/146; 514/307, 514/213.01, 412; 540/593; 548/503

[56] References Cited

U.S. PATENT DOCUMENTS 4,022,900 5/1977 Mathison .................... 424/258

FOREIGN PATENT DOCUMENTS 984517 2/1965 United Kingdom .

OTHER PUBLICATIONS

Mathison, et al., "Synthesis and Hypotensive Properties of Tetrahydroisoquinolines", (1973), Journal of Medicinal Chemistry, vol. 18, No. 4, pp. 332–336.

*Primary Examiner*—Zinna Northington Davis
*Attorney, Agent, or Firm*—Linda E. Hall; Stephen A. Venetianer; Charles M. Kinzig

[57] ABSTRACT

This invention relates to substituted benzamido-heterocyclic compounds of general formula (I) having an alkoxy substituent at the C2 position of the benzamido group and various substituents at positions C4 and C5, being optionally substituted on the N atom of the heterocyclic system, and where the unsaturated ring of the heterocyclic system is a 5,6, 7 or 8-membered ring. Also to the use of these compounds as anticonvulsants in certain medical conditions, and to processes for making them.

20 Claims, No Drawings

SUBSTITUTED BENZAMIDE DERIVATIVES AND THEIR USE AS ANTICONVULSANTS

This application is a 371 of PCT/EP97/03131, filed Jun. 13, 1997.

This invention relates to novel compounds, to processes for preparing them, and to their use as therapeutic agents.

U.S. Pat. No. 4,022,900 (Marion), FR-A-2004748 (Marion) and DE-A-2101691 (Marion) disclose benzamido-tetrahydroisoquinolines having anti-hypertensive and vasodilator properties, including the compound 5-(2,4,5-trimethoxy-benzamido)-2-methyl-1,2,3,4-tetrahydroisoquinolin, which can also be expressed as 2,4,5-trimethoxy-N-(2-methyl-1,2,3,4-tetrahydroisoquinolin-5-yl)benzamide.

It as now been surprisingly found that benzamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, and amyotrophic lateral sclerosis (ALS).

Accordingly, the present invention provides a compound of formula (I) or pharmaceutically acceptable salt thereof:

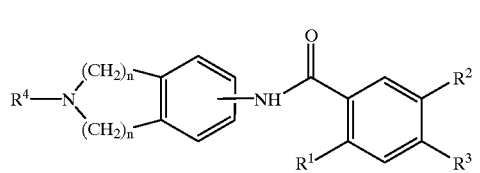

(I)

where n and p are independently integers from 1 to 4 and (n+p) is from 2 to 5;

$R^1$ is $C_{1-6}$alkylO-;

$R^2$ is hydrogen, halogen, CN, $N_3$, trifluoromethyldiazirinyl, $CF_3$, $CF_3O-$, $CF_3S-$, $CF_3CO-$, $C_{1-6}$alkyl, $C_{3-6}$cycloalkyl, $C_{3-6}$cycloalkyl-$C_{1-4}$alkyl-, $C_{1-6}$alkylO-, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-, $C_{1-6}$alkylS-, $C_{1-6}$alkylSO$_2$—, $(C_{1-4}$alkyl$)_2$NSO$_2$— or $(C_{1-4}$alkyl)NHSO$_2$—;

$R^3$ is hydrogen, halogen, $NO_2$, CN, $N_3$, trifluoromethyldiazirinyl, $C_{1-6}$ alkylO-, $C_{1-6}$ alkylS-, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO-$, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-, or —NR$^5$R$^6$ were R$^5$ is hydrogen or $C_{1-4}$ alkyl, and R$^6$ is hydrogen, $C_{1-4}$alkyl, —CHO, —CO$_2C_{1-4}$alkyl or —COC$_{1-4}$alkyl;

$R^4$ is hydrogen, $C_{1-6}$ alkyl, $C_{1-6}$ alkenyl, or $C_{1-6}$ alkynyl; but excluding the compound 2,4,5-trimethoxy-N-(2-methyl-1,2,3,4-tetrahydroisoquinolin-5-yl)benzamide.

The compounds of this invention are typically (tetrahydroisoquinolin-5-yl)benzamides, (tetrahydroisoquinolin-6-yl)benzamides, (tetrahydroisoquinolin-7-yl)benzamides or (tetrahydroisoquinolin-8-yl)benzamides, especially (tetrahydroisoquinolin-7-yl)benzamides, and most suitably (tetrahydroisoquinolin-5-yl)benzamides; or (dihydroisoindol-4-yl)benzamides; or (tetrahydro-3-benzazepin-6-yl)benzamides.

In the formula (I), $R^1$ alkoxy groups are typically based on straight chain alkyl groups, but in general alkyl groups may be straight chain or branched. Aromatic rings, especially the aromatic ring in the bicyclic heterocyclic moiety in formula (I) and phenyl groups, including phenyl groups that are part of other moieties, in $R^2$ and $R^3$ may optionally be substituted with one or more independently selected halogen or $C_{1-6}$ alkyl, $C_{1-6}$ alkoxy or $C_{1-6}$ alkylcarbonyl.

Suitable $C_{3-6}$ cycloalkyl groups include cyclopropyl, cyclobutyl, cyclopentyl, and cyclohexyl.

Suitable halo substituents include fluoro, chloro, iodo and bromo.

A suitable group of compounds of formula (I) have $R^1$ as methoxy, ethoxy or n-propoxy $R^2$ as hydrogen, methoxy, bromo, chloro, iodo, acetyl, pivaloyl, iso-butyroyl, benzoyl, trifluoromethyl, trifluoroacetyl, n-propylsulfonyl, isopropylsulfonyl or dimethylsulfamoyl $R^3$ as hydrogen, methyl, ethyl, n-butyl, iso-propyl, t-butyl, phenyl, methoxy, ethoxy, iso-propoxy, n-butoxy, phenoxy, benzyloxy, amino, acetylamino, nitro, benzoyl, iodobenzoyl, chloro or azido $R^4$ as hydrogen, methyl, ethyl or propyl.

In a special class of compounds of formula (I), suitable for use as mechanistic probes, $R^2$ or $R^3$ are photolabile groups, such as $N_3$, benzoyl and trifluoromethyldiazirinyl. Also radiolabels such as $^{125}I$ can be incorporated at $R^2$ or $R^3$, and $^3H$ and $^{125}I$ can be located at other suitable positions.

Examples of compounds of formula (I) are:

N-(2-methyl-1,2,3,4-tetrahydroisoquinolin-5-yl)-4-amino-5-chloro-2-methoxybenzamide N-(2-methyl-1,2,3,4-tetrahydroisoquinolin-5-yl)-2,4-dimethoxybenzamide N-(2-methyl-1,2,3,4-tetrahydroisoquinolin-5-yl)-2-methoxybenzamide N-(2-methyl-1,2,3,4-tetrahydroisoquinolin-5-yl)-5-chloro-2-methoxybenzamide N-(2-methyl-1,2,3,4-tetrahydroisoquinolin-5-yl)-4-chloro-2-methoxybenzamide N-(2-methyl-1,2,3,4-tetrahydroisoquinolin-5-yl)-4-acetylamino-5-bromo-2-methoxybenzamide N-(2-methyl-1,2,3,4-tetrahydroisoquinolin-5-yl)-4-amino-5-bromo-2-methoxybenzamide N-(2-methyl-1,2,3,4-tetrahydroisoquinolin-5-yl)-4-azido-5-iodo-2-methoxybenzamide N-(2-methyl-1,2,3,4-tetrahydroisoquinolin-5-yl)-4-acetylamino-5-chloro-2-propoxybenzamide N-(2-methyl-1,2,3,4-tetrahydroisoquinolin-5-yl)-4-amino-5-chloro-2-propoxybenzamide N-(2-methyl-1,2,3,4-tetrahydroisoquinolin-5-yl)-4-acetylamino-2-methoxybenzamide N-(2-methyl-1,2,3,4-tetrahydroisoquinolin-5-yl)-5-chloro-2-methoxy-4-nitrobenzamide N-(2-methyl-1,2,3,4-tetrahydroisoquinolin-5-yl)-4-amino-5-iodo-2-methoxybenzamide N-(2-methyl-1,2,3,4-tetrahydroisoquinolin-5-yl)-4-benzyloxy-5-chloro-2-methoxybenzamide
N-(2-methyl-1,2,3,4-tetrahydroisoquinolin-5-yl)-4,5-dichloro-2-methoxybenzamide
N-(2-methyl-1,2,3,4-tetrahydroisoquinolin-5-yl)-5-chloro-2,4-dimethoxybenzamide
N-(2-methyl-1,2,3,4-tetrahydroisoquinolin-5-yl)-5-bromo-2,4-dimethoxybenzamide
N-(2-methyl-1,2,3,4-tetrahydroisoquinolin-5-yl)-5-[3-(trifluoromethyl)-3H-diazirin-3-yl]-2-methoxybenzamide
N-(1,2,3,4-tetrahydroisoquinolin-5-yl)-5-chloro-2,4-dimethoxybenzamide
N-(2-methyl-1,2,3,4-tetrahydroisoquinolin-5-yl)-5-chloro-2-methoxy-4-methylbenzamide
N-(2-n-propyl-1,2,3,4-tetrahydroisoquinolin-5-yl)-5-chloro-2,4-dimethoxybenzamide
N-(2-ethyl-1,2,3,4-tetrahydroisoquinolin-5-yl)-5-chloro-2,4-dimethoxybenzamide
N-(2-methyl-1,2,3,4-tetrahydroisoquinolin-5-yl)-5-chloro-4-ethoxy-2-methoxybenzamide
N-(2-methyl-1,2,3,4-tetrahydroisoquinolin-5-yl)-2,5-dimethoxybenzamide
N-(2-methyl-1,2,3,4-tetrahydroisoquinolin-5-yl)-5-bromo-2-methoxy-4-methylbenzamide
N-(2-methyl-1,2,3,4-tetrahydroisoquinolin-5-yl)-5-dimethylsulfamoyl-2-methoxybenzamide
N-(2-methyl-1,2,3,4-tetrahydroisoquinolin-5-yl)-4-benzoyl-2-methoxybenzamide
N-(2-methyl-1,2,3,4-tetrahydroisoquinolin-5-yl)-5-benzoyl-2-methoxybenzamide
N-(2-methyl-1,2,3,4-tetrahydroisoquinolin-8-yl)-4-acetylamino-5-chloro-2-methoxybenzamide
N-(2-methyl-1,2,3,4-tetrahydroisoquinolin-8-yl)-4-amino-5-chloro-2-methoxybenzamide
N-(2,3-dihydro-2-methyl-1H-isoindol-4-yl)-5-chloro-2,4-dimethoxybenzamide.
N-(3-methyl-2,3,4,5-tetrahydro-1H-3-benzazepine-6-yl)-4-tert-butyl-2-methoxy-benzamide
N-(1,2,3,4-tetrahydroisoquinolin-6-yl)-4-tert-butyl-2-methoxybenzamide
N-(2-methyl-1,2,3,4-tetrahydroisoquinolin-6-yl)-4-tert-butyl-2-methoxybenzamide
N-(2-methyl-1,2,3,4-tetrahydroisoquinolin-5-yl)-4-tert-butyl-2-methoxybenzamide
N-(2-methyl-1,2,3,4-tetrahydroisoquinolin-5-yl)-4-n-butyl-2-methoxy-5-chloro-benzamide
N-(2-methyl-1,2,3,4-tetrahydroisoquinolin-5-yl)-4-ethyl-2-methoxy-5-chloro benzamide
N-(2-methyl-1,2,3,4-tetrahydroisoquinolin-5-yl)-4-tert-butyl-2-methoxy-5-chloro-benzamide
N-(2-methyl-1,2,3,4-tetrahydroisoquinolin-5-yl)-2-methoxy-4-phenylbenzamide
N-(1,2,3,4-tetrahydroisoquinolin-5-yl)-4-tert-butyl-2-methoxybenzamide
N-(2-methyl-1,2,3,4-tetrahydroisoquinolin-5-yl)-4-iso-propyl-2-methoxybenzamide
N-(2-methyl-1,2,3,4-tetrahydroisoquinolin-5-yl)-5-chloro-4-iso-propyl-2-methoxybenzamide
N-(1,2,3,4-tetrahydroisoquinolin-5-yl)-5-chloro-4-tert-butyl-2-methoxybenzamide
N-(2-methyl-1,2,3,4-tetrahydroisoquinolin-5-yl)-4-ethyl-2-methoxybenzamide
N-(2-methyl-1,2,3,4-tetrahydroisoquinolin-5-yl)-5-bromo-4-iso-propoxy-2-methoxybenzamide
N-(2-methyl-1,2,3,4-tetrahydroisoquinolin-5-yl)-4-iso-propyl-5-trifluoromethyl-2-methoxybenzamide
N-(2-methyl-1,2,3,4-tetrahydroisoquinolin-5-yl)-4-iso-propoxy-2-methoxy-5-trifluoromethyl-benzamide
N-(2-methyl-1,2,3,4-tetrahydroisoquinolin-5-yl)-5-bromo-4-iso-propyl-2-methoxybenzamide
N-(2-methyl-1,2,3,4-tetrahydroisoquinolin-5-yl) 5-iso-butyroyl-2-methoxy-benzamide
N-(2-methyl-1,2,3,4-tetrahydroisoquinolin-5-yl)-5-pivaloyl-2-methoxybenzamide
N-(2-methyl-1,2,3,4-tetrahydroisoquinolin-7-yl)-5-chloro-2-methoxy-4-iso-propoxybenzamide
N-(2-methyl-1,2,3,4-tetrahydroisoquinolin-7-yl)-5-bromo-2,4-dimethoxybenzamide
N-(2-methyl-1,2,3,4-tetrahydroisoquinolin-7-yl)-4-tert-butyl-2-methoxybenzamide
N-(2-methyl-1,2,3,4-tetrahydroisoquinolin-7-yl)-2-methoxy-4-methyl-5-trifluoromethylbenzamide
N-(2-methyl-1,2,3,4-tetrahydroisoquinolin-7-yl)-2-methoxybenzamide
N-(2-methyl-1,2,3,4-tetrahydroisoquinolin-7-yl)-2,4-dimethoxybenzamide
N-(2-methyl-1,2,3,4-tetrahydroisoquinolin-7-yl)-5-chloro-2-methoxybenzamide
N-(2-methyl-1,2,3,4-tetrahydroisoquinolin-5-yl)-4-iso-propoxy-2-methoxybenzamide
N-(2-methyl-1,2,3,4-tetrahydroisoquinolin-5-yl)-5-dimethylsulfamoyl-2,4-dimethoxybenzamide
N-(2-methyl-1,2,3,4-tetrahydroisoquinolin-5-yl)-2-methoxy--iso-propylsulfonylbenzamide
N-(2-methyl-1,2,3,4-tetrahydroisoquinolin-5-yl)-5-chloro-2-methoxy-4-phenylbenzamide
N-(1,2,3,4-tetrahydroisoquinolin-5-yl)-5-bromo-2,4-dimethoxybenzamide
N-(2-methyl-1,2,3,4-tetrahydroisoquinolin-5-yl)-2-methoxy-5-n-propylsulfonylbenzamide
N-(2-methyl-1,2,3,4-tetrahydroisoquinolin-5-yl)-2,4-dimethoxy-5-trifluoromethylbenzamide
N-(2-methyl-1,2,3,4-tetrahydroisoquinolin-5-yl)-2-methoxy-4-methyl-5-trifluoromethylbenzamide
N-(2-methyl-1,2,3,4-tetrahydroisoquinolin-5-yl)-5-acetyl-2,4-dimethoxybenzamide
N-(2-methyl-1,2,3,4-tetrahydroisoquinolin-5-yl)-5-bromo-4-ethyl-2-methoxybenzamide
N-(2-methyl-1,2,3,4-tetrahydroisoquinolin-5-yl)-4-ethyl-2-methoxy-5-trifluoromethylbenzamide
N-(2-methyl-1,2,3,4-tetrahydroisoquinolin-5-yl)-4-n-butoxy-5-chloro-2-methoxybenzamide
N-(2-methyl-1,2,3,4-tetrahydroisoquinolin-5-yl)-2-methoxy-4-iso-propyloxy-5-acetyl-benzamide
N-(2-methyl-1,2,3,4-tetrahydroisoquinolin-5-yl)-5-chloro-2-methoxy-4-iso-propoxybenzamide
N-(2-methyl-1,2,3,4-tetrahydroisoquinolin-5-yl)-2-methoxy-5-iodo-4-trifluoromethyldiazirinyl benzamide
N-(1,2,3,4-tetrahydroisoquinolin-5-yl)-4-azido-5-iodo-2-methoxybenzamide
N-(1,2,3,4-tetrahydroisoquinolin-5-yl)-5-iodo-2-methoxy-4-trifluoromethyldiazirinylbenzamide
N-(7-iodo-2-methyl-1,2,3,4-tetrahydroisoquinolin-5-yl)-5-benzoyl-2-methoxybenzamide
N-(7-iodo-1,2,3,4-tetrahydroisoquinolin-5-yl)-5-benzoyl-2-methoxybenzamide
N-(5-iodo-1,2,3,4-tetrahydroisoquinolin-7-yl)-5-benzoyl-2-methoxybenzamide
N-(5-iodo-1,2,3,4-tetrahydroisoquinolin-7-yl)-2-methoxy-4-trifluoromethyldiazirinylbenzamide
N-(5-iodo-1,2,3,4-tetrahydroisoquinolin-7-yl)-2-methoxy-5-trifluoromethyldiazirinylbenzamide
N-(2-methyl-1,2,3,4-tetrahydroisoquinolin-5-yl)-2-methoxy-5-trifluoroacetyl benzamide
N-(2-methyl-1,2,3,4-tetrahydroisoquinolin-5-yl)-2-methoxy-4-trifluoromethyldiazirinylbenzamide N-(1,2,3,4-tetrahydroisoquinolin-7-yl)-5-iodo-2-methoxy-4-trifluoromethyldiazirinylbenzamide N-(1,2,3,4-tetrahydroisoquinolin-5-yl)-5-(4-iodobenzoyl)-2-methoxybenzamide N-(7-iodo-1,2,3,4-tetrahydroisoquinolin-5-yl)-2-methoxy-5-trifluoromethyldiazirinylbenzamide, N-(2-Methyl-1,2,3,4-tetrahydroisoquinolin-7-yl)-4-chloro-2-methoxybenzamide N-(2-Methyl-1,2,3,4-tetrahydroisoquinolin-7-yl)-2-methoxy-4-methylthiobenzamide N-(8-Fluoro-2-methyl-1,2,3,4-tetrahydroisoquinolin-5-yl)-4-t-butyl-2-methoxybenzamide N-(2-Methyl-1,2,3,4-tetrahydroisoquinolin-5-yl)-5-iso-butyroyl-4-iso-propoxy-2-methoxybenzamide, and N-(2-methyl-1,2,3,4-tetrahydroisoquinolin-5-yl)-4-n-butoxy-2-methoxybenzamide.

A preferred group of these compounds is

N-(2-methyl-1,2,3,4-tetrahydroisoquinolin-5-yl)-4-amino-5-chloro-2-methoxybenzamide N-(2-methyl-1,2,3,4-tetrahydroisoquinolin-5-yl)-4-amino-5-bromo-2-methoxybenzamide N-(2-methyl-1,2,3,4-tetrahydroisoquinolin-5-yl)-4-amino-5-iodo-2-methoxybenzamide N-(2-methyl-1,2,3,4-tetrahydroisoquinolin-5-yl)-5-chloro-4-ethoxy-2-methoxybenzamide N-(2-methyl-1,2,3,4-tetrahydroisoquinolin-7-yl)-5-bromo-2,4-dimethoxybenzamide N-(2-methyl-1,2,3,4-tetrahydroisoquinolin-5-yl)-4-tert-butyl-2-methoxybenzamide N-(2-methyl-1,2,3,4-tetrahydroisoquinolin-5-yl)-5-bromo-4-iso-propoxy-2-methoxy-benzamide N-(2-methyl-1,2,3,4-tetrahydroisoquinolin-5-yl)-4-iso-propyl-5-trifluoromethyl-2-methoxybenzamide N-(2-methyl-1,2,3,4-tetrahydroisoquinolin-5-yl) 5-iso-butyroyl-2-methoxy-benzamide N-(2-methyl-1,2,3,4-tetrahydroisoquinolin-5-yl)-5-pivaloyl-2-methoxybenzamide N-(2-methyl-1,2,3,4-tetrahydroisoquinolin-5-yl)-2-methoxy-4-iso-propyloxy-5-acetyl-benzamide N-(2-methyl-1,2,3,4-tetrahydroisoquinolin-5-yl)-5-chloro-2-methoxy-4-iso-propoxybenzamide.

N-(2-Methyl-1,2,3,4-tetrahydroisoquinolin-5-yl)-4-ethyl-2-methoxy-5-chlorobenzamide, hydrochloride N-(2-Methyl-1,2,3,4-tetrahydroisoquinolin-5-yl)-4-ethyl-2-methoxy-5-trifluoromethylbenzamide, hydrochloride When synthesised, these compounds are often in salt form, typically the hydrochloride or trifluoroacethate, and such salts also form part of this invention. Such salts may be used in preparing pharmaceutically acceptable salts. The compounds and their salts may be obtained as solvates, such as hydrates, and these also form part of this invention.

The above-listed compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 60, 80, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical, nasal, or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or nasal sprays or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbithan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substhantially the same manner except that the compound is suspended in the vehicle instead of being dissolved and sterilised by exposure to ethylene oxide before suspending in the sterile vehicle. Advantageously, a surfacthant or wetting agent is included in the composition to facilithate uniform distribution of the compound of the invention.

As is common practice, the compositions will usually be accompanied by written or printed directions for use in the medical treatment concerned.

Accordingly, in a further aspect, the present invention provides a pharmaceutical composition for use in the treatment and/or propylaxis of anxiety, mania, depression, panic disorders and/or aggression, disorders associated with a subarachnoid haemorrhage or neural shock, the effects associated with withdrawal from substhances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated withh AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, and amyotrophic lateral sclerosis (ALS) which comprises a compound of formula (I), withhout excluding 2,4,5-trimethoxy-N-(2-methyl-1,2,3,4-tetrahydroisoquinolin-5-yl)benzamide, or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substhances of abuse such as cocaine, nicotine, alcohol and benzodiazepines, disorders treatable and/or preventable with anti-convulsive agents, such as epilepsy including post-traumatic epilepsy, Parkinson's disease, phychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, and amyotrophic lateral sclerosis (ALS) comprising administering to the sufferer in need thereof an effective or prophylactic amount of a compound of formula (I), without excluding 2,4,5-trimethoxy-N-(2-methyl-1,2,3,4-tetrahydroisoquinolin-5-yl)benzamide, or a pharmaceutically acceptable salt or solvate thereof.

In a further aspect the invention provides the use of a compound of formula (I), without excluding 2,4,5-trimethoxy-N-(2-methyl-1,2,3,4-tetrahydroisoquinolin-5-yl)benzamide, or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substhances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substhances of abuse such as cocaine, nicotine, alcohol and benzodiazepines, disorders treatable and/or preventable with anti-convulsive agents, such as epilepsy including post-traumatic epilepsy, Parkinson's disease, phychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, and amyotrophic lateral sclerosis (ALS).

Another aspect of the invention provides a process for the preparation of compounds of formula (I), which comprises reacting a compound of formula (II)

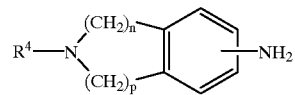

(II)

where n and p are as defined for formula (I) and $R^{4A}$ is $R^4$ as defined for formula (I) or a group convertible to $R^4$ with a compound of formula (III)

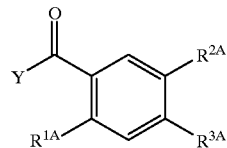

(III)

where Y is Cl or OH, and $R^{1A}$, $R^{2A}$, and $R^{3A}$ are respectively $R^1$, $R^2$, and $R^3$ as defined for formula (I) or groups convertible to $R^1$, $R^2$, and $R^3$, and were required converting a $R^{1A}$, $R^{2A}$, $R^{3A}$ or $R^{4A}$ group to a $R^1$, $R^2$, $R^3$ or $R^4$ group, converting one $R^1$, $R^2$, $R^3$ or $R^4$ group to another $R^1$, $R^2$, $R^3$ or $R^4$ group, converting a hydrochloride salt product to the free base or another pharmaceutically acceptable salt or converting a free base product to a pharmaceutically acceptable salt.

Reaction of a compound of formula (III) which is a benzoyl chloride derivative (Y=Cl) will lead directly to the hydrochloride salt. Suitable solvents include ethyl acetate and tetrahydrofuran. When the compound of formula (III) is a benzoic acid derivative (Y=OH), conventional conditions for condensation of aromatic acids with amines may be used, for example reacting the components in a mixture of (dimethylaminopropyl)-ethyl-carbodiimide and hydroxybenzotriazole in a suitable solvent such as dimethyl formamide.

Conversions of an $R^{1A}$, $R^{2A}$, $R^{3A}$ or $R^{4A}$ group to a $R^1$, $R^2$; $R^3$ or $R^4$ group typically arise when a protecting group is needed during the above coupling reaction or during the preparation of the reactants by the procedures described below. Interconversion of one $R^1$, $R^2$, $R^3$ or $R^4$ group to another typically arises when one compound of formula (I) is used as the immediate precursor of another compound of formula (I) or when it is easier to introduce a more complex or reactive substituent at the end of a synthetic sequence.

Compounds of formula (II) may be prepared from a compound of formula (IV)

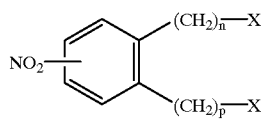

(IV)

where X is a leaving group, such as halogen, especially Br, or methanesulfonyl, which is reacted with $R^{4A}NH_2$, were $R^{4A}$ is $R^4$ as defined above or an N-protecting group, to obtain compounds of formula (V)

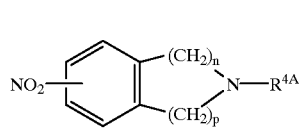

(V)

and then reduced, for example using hydrogen/palladium, to obtain compounds of formula (II).

Alternatively, a compound of formula (VI)

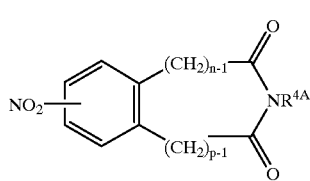

(VI)

may be reduced directly, for example with lithium aluminium hydride, typically in tetrahydrofuran, to obtain a compound of formula (II) or a compound of formula (II) may obtained in a two step procedure were a hydrogenation, typically with hydrogen/palladium, is followed by reduction, again suitably with lithium aluminium hydride.

When $R^{4A}$ in formula (V) or (VI) is alkenyl or alkynyl, reagents for reduction of $NO_2$ must be selected so as to selectively reduce $NO_2$ without affecting the $R^{4A}$ group. It may be more suitable that $R^{4A}$ in formula (V) or (VI) is an N-protecting group, that may be removed at an appropriate point in the reaction and replaced by a desired $R^4$ group by conventional methods.

Compounds of formulae (UV) and (VI) and the reagents used are commercially available, or can be prepared from commercially available materials using conventional procedures described in the literature, and as illustrated below.

More specifically, compounds of formula (II) in which n=1 and p=2 or n=2 and p=1 are tetrahydroisoquinolines and may be prepared from the corresponding unsaturated compound of formula (VII)

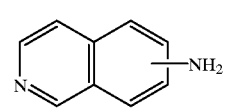

(VII)

by reaction with a compound $R^{4A}Z$ were Z is a leaving group such as halogen, especially iodo, or tosylate to obtain an intermediate of formula (VIII)

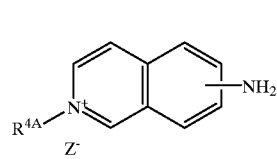

(VIII)

which can be reduced, for example using sodium borohydride, to the compound of formula (II). Alternatively the compound of formula (VIII) can be hydrogenated, for example using hydrogen at 50 psi in a solution of acetic/sulphuric acid with a platinum oxide catalyst.

Another route is from a precursor of formula (IX)

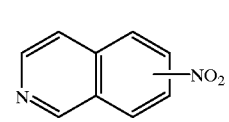

(IX)

which can be reacted with $R^{4A}Z$, preferably as a tosylate, to obtain the intermediate of formula (X)

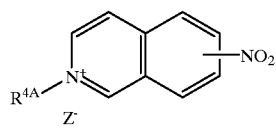

(X)

which can then be hydrogenated under the conditions previously described to prepare the compound of formula (II).

When $R^{4A}$ is hydrogen, the compound of formula (II) can be obtained by direct hydrogenation of the compounds of formula (VII) or (IX), using the reagents already described. The NH may be protected conventionally, for example by making $R^{4A}$ t-butoxycarbonyl, prior to formation of the benzamide, and then deprotected under sthandard conditions, for example using trifluoroacetic acid/methylene chloride.

Compounds of formulae (VII) and (IX) and the reagents used are commercially available, or can be prepared from commercially available materials using conventional procedures described in the literature.

Compounds of formula (II) in which n=1 and p=1 are amino-dihydroisoindolines. Such compounds may be prepared from compounds of formula (XI)

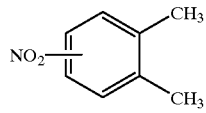
(XI)

by forming a leaving group, such as bromo, on the methyl groups, and reacting with an amine $R^{4A}NH_2$ to form the saturated heterocyclic ring, followed by reduction of the nitro group. For example, the compound of formula (XII)

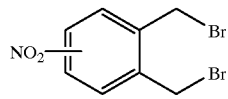
(XII)

may be formed by refluxing the compound of formula (XI) with N-bromosuccinimide/carbon tetrachloride in the presence of a light source and/or a radical initiator such as t-butyl perbenzoate. The product (XII) can be reacted with $R^{4A}NH_2$ in methylene dichloride to obtain the compound of formula (XIII)

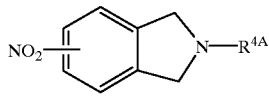
(XIII)

This can be converted to an aminoisoindoline of formula (II) by reduction with hydrogen and a palladium catalyst in ethanol. This route is based on the procedure disclosed in U.S. Pat. No. 5,436,250.

Alternative routes to dihydroisoindolines of formula (II) via a compound of formula (VI) were n=1 and p=1 can be found in Wätjen et al, Biomed. Lett. 1994, 4(2), 371 and Knefeli et al, Arch. Pharm. 1989, 322, 419.

Compounds of formula (II) in which (n+p)=4 are amino-tetrahydrobenzazepines. Such compounds may be prepared from a compound of formula (XIV)

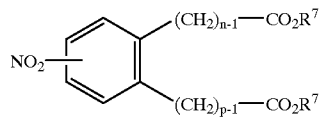
(XIV)

where $R^7$ is $C_{1-4}$alkyl, typically methyl or ethyl, which is reacted with diborane in a suitable solvent such as tetrahydrofuran to give a compound of formula (XV)

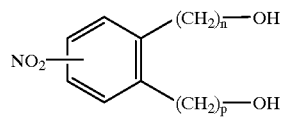
(XV)

Further reaction with methanesulfonyl chloride in pyridine gives a compound of formula (XVI)

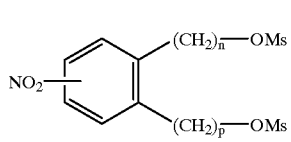
(XVI)

which is a compound of formula (IV) in which X is methanesulfonyl (OMs). This can be reacted with $R^{4A}NH_2$ in a solvent such as dimethylformamide to obtain a compound of formula (V) with the appropriate n/p values for an amino-tetrahydrobenzazepine.

In this reaction $R^{4A}$ is suitably a protecting group such as benzyl which is easily replaceable by desired $R^4$ groups. Further reaction with hydrogen and a palladium catalyst in acetic acid converts the $NO_2$ group to $NH_2$ and results in a compound of formula (II). If the $R^{4A}$ group in formula (XVII) is benzyl then the corresponding formula (II) compound will contain a $R^4$ hydrogen group, which can be used as a starting point for additional $R^4$ groups by conventional interconversions. This reaction scheme is based on the disclosure of EP-A-0002624 to which reference is directed, and which specifically discloses preparation of aminotetrahydrobenzazepines of formula (II) in which n=1 and p=3 (or vice versa), or as described by R. M. DeMarinis et al, J. Med. Chem., 1984, 27, 918 for n=p=2.

Compounds of formula (III) can be prepared by further substitution of commercially available benzoic acid derivatives using conventional procedures, by analogy with the procedures set out in the Preparations below. Suitable starting materials are 2,4-dimethoxy benzoic acid, 2-methoxy 4-amino benzoic acid and 2-methoxy 4-chloro benzoic acid.

The preparation of compounds of this invention is further illustrated by the following Preparations and Examples. The utility of compounds of this invention is shown by the Pharmacological Data that follow the Examples.

PREPARATION 1

5-Amino-2-methylisoquinolinium Iodide

To a solution of 5-aminoisoquinoline (14.4 g, 100 mmol) in acetone (300 ml) was added iodomethane (14.4 ml). The solution was briefly stirred and then allowed to sthand for 2h. The yellow precipithate was then filtered, washed with acetone and dried to afford the title compound as a yellow solid (18.8 g).

PREPARATION 2

5-Amino-2-methyl-1,2,3,4-tetrahydroisoquinoline

To an ice cold solution of 5-amino-2-methylisoquinolinium iodide (18.8 g, 65 mmol) in methanol (1.5L) and water (60 ml) was added sodium borohydride (17.8 g, 0.47 mol) portionwise over 2h. The mixture was then allowed to stir at room temperature for 18h before concentration in vacuo and partitioning of the residue between water and dichloromethane. The organic layer was dried over sodium sulfate and concentrated in vacuo to afford the title compound (8.87 g).

PREPARATION 3

4-Azido-5-iodo-2-methoxybenzoic Acid

To a solution of 4-amino-5-iodo-2-methoxybenzoic acid (300 mg, 1.02 mmol) in trifluoroacetic acid (4 ml) at 5° C., was added sodium nitrite (283 mg, 4.1 mmol) portionwise, and the mixture allowed to stir for 30 min. Sodium azide (200 mg, 3.07 mmol) was then added portionwise and the mixture stirred for a further 30 min at 0° C. The mixture was diluted with water, and a yellow solid precipithated. The solid was filtered, washed with cold water and dried, to afford the title compound (274 mg, 84%).

PREPARATION 4

4,5-Dichloro-2-methoxybenzoic Acid

To an ice cold solution of 4-chloro-2-methoxybenzoic acid (1.0 g, 5.36 mmol) in trifluoroacetic acid (7 ml) was added N-chloromorpholine (0.67 g, 5.5 mmol) dropwise, maintaining the internal temperature below 10° C. After stirring overnight at room temperature the trifluoroacetic acid was removed in vacuo and the residue partitioned between ethyl acetate and water. The organic layer was dried over magnesium sulfate, concentrated in vacuo and the residue recrystallised from methanol to afford the title compound as a white solid (200 mg).

PREPARATION 5

5-Chloro-2,4-dimethoxybenzoic Acid

The title compound was prepared in an analogous fashion to Preparation 4 from 2,4-dimethoxybenzoic acid (1.3 g). Recrystallisation of the crude product from methanol afforded the title compound as a white solid (1.3 g).

PREPARATION 6

5-Bromo-2,4-dimethoxybenzoic Acid

To a solution of 2,4-dimethoxybenzoic acid (4.0 g, 0.022 mol) in chloroform (60 ml) was added bromine (1.13 ml, 0.022 mol) in chloroform (20 ml) dropwise. After stirring overnight at room temperature the precipithate was filtered off and dried to afford the title compound as a white solid (2.87 g).

PREPARATION 7

(5-Bromo-2-methoxybenzyloxy)-tert-butyldimethylsilane

To a solution of 5-bromo-2-methoxybenzyl alcohol (1.0 g, 4.6 mmol) and imidazole (470 mg, 7.01 mmol) in DMF (15 ml) was added tert-butyldimethylsilyl chloride (1.04 g, 6.91 mmol). The mixture was allowed to stir for 4 h, poured onto water (100 ml) and extracted with ether (3×30 ml). The combined organic phases were washed with water (50 ml), brine (50 ml), dried over sodium sulfate and evaporated under reduced pressure to leave a pale yellow oil. This was purified by chromatography ($SiO_2$, 5% ether/petrol), to give the title compound (1.46 g, 96%) as a colourless oil.

PREPARATION 8

(5-Trifluoroacetyl-2-methoxybenzyloxy)-tert-butyldimethylsilane

To a solution of 5-bromo-2-methoxybenzyloxy)-tert-butyldimethylsilane (1.0 g, 3.02 mmol) in THF (5 ml) at −78° C., was added n-BuLi (2.26 ml of a 1.6 M solution in penthane, 3.62 mmol) dropwise over 10 min. The solution was allowed to stir for a further 1 h at −78° C., to give a bright yellow solution. N,N-diethyltrifluoroacetamide (561 mg, 3.32 mmol) in THF (2 ml) was added dropwise over 30 min, and the solution was stirred for a further 1 h at −78° C. Saturated aqueous ammonium chloride (5 ml) was added and the mixture allowed to warm to room temperature, and extracted with ether (3×10 ml). The combined organic phases were washed with water (10 ml), brine (10 ml), dried over sodium sulfate and evaporated in vacuo. The resulting residue was purified by chromatography ($SiO_2$, 5% ether/petrol) to give the title compound (0.99 g, 94%) as a white solid.

PREPARATION 9

(E, Z)-1-[3-(tert-Butyldimethylsilanyloxymethyl)-4-methoxyphenyl]-2,2,2-trifluoroethanone Oxime A mixture of (5-trifluoroacetyl-2-methoxybenzyloxy)-tert-butyldimethylsilane (1.0 g, 2.87 mmol), hydroxylamine hydrochloride (240 mg, 3.44 mmol), pyridine (18 ml) and ethanol (9 ml) were heated at reflux for 4 h. The resulting mixture was evaporated in vacuo and the residue purified by chromatography ($SiO_2$, 20% ether/petrol), to give an approximately 3:2 inseparable isomeric mixture of (E, Z)-1-[3-(tert-butyldimethylsilanyl oxymethyl)-4-methoxyphenyl]-2,2,2-trifluoroethanone oximes (1.02 g, 98%) as a colourless oil.

PREPARATION 10

(E, Z)-(4-Toluensulfonyl)-1-[3-(tert-butyldimethylsilanyloxymethyl)-4-methoxy phenyl]-2,2,2-trifluoroethanone Oxime To a solution of (E, Z)-1-[3-(tert-butyldimethylsilanyloxymethyl)-4-methoxyphenyl]-2,2,2-trifluoroethanone oximes (1.0 g, 2.75 mmol), triethylamine (340 mg, 3.36 mmol), DMAP (31 mg, 0.25 mmol) in dichloromethane (5 ml) at 0° C., was added tosyl chloride (627 mg, 3.29 mmol) portionwise. The mixture was stirred for 1 h at room temperature and then poured onto water (10 ml). The layers were separated, and the aqueous phase extracted with dichloromethane (3×10 ml). The combined organic phases were washed with water (10 ml), dried ($Na_2SO_4$) and evaporated in vacuo. The residue was purified by chromatography ($SiO_2$, 20% ether/petrol) to give an inseparable mixture of (E, Z)-(4-toluensulfonyl)-1-[3-(tert-butyldimethylsilanyloxymethyl)-4-methoxyphenyl]-2,2,2-trifluoroethanone oximes (1.39 g, 98%) as a colourless oil.

PREPARATION 11

3-[3-(tert-Butyldimethylsilanyloxymethyl)-4-methoxyphenyl]-3-trifluoromethyldiaziridine A solution of (E, Z)(4-toluensulfonyl)-1-[3-(tert-butyldimethylsilanyloxymethyl)-4-methoxyphenyl]-2,2,2-trifluoroethanone oximes (517 mg, 1 mmol) in ether (5 ml) was stirred with liquid $NH_3$ (15 ml) in a bomb for 4 h at room temperature. The mixture was then filtered and the solid washed with ether. The filtrate was evaporated in vacuo and the residue purified by chromatography ($SiO_2$, 20% ether/petrol) to give the title compound (350 mg, 97%) as a pale yellow oil.

PREPARATION 12

3-[3-(tert-Butyldimethylsilanyloxymethyl)-4-methoxyphenyl]-3-trifluoromethyl-3H-diazirine A mixture of 3-[3-(tert-butyldimethylsilanyloxymethyl)-4-methoxyphenyl]-3-trifluoromethyldiaziridine (200 mg, 0.55 mmol) and freshly prepared Ag$_2$O(255 mg, 1.1 mmol) in ether (3 ml) was stirred for 24 h. The solid was filtered, washed with ether, and the filtrate evaporated in vacuo. The resulting residue was purified by chromatography (SiO$_2$, 10% ether/petrol) to give the title compound (187 mg, 94%) as a colourless oil.

PREPARATION 13

2-Methoxy-5-(3-trifluoromethyl-3H-diazirin-3-yl) benzoic Acid

A solution of 3-[3 -(tert-butyldimethylsilanyloxymethyl)-4-methoxyphenyl]-3-trifluoromethyl-3H-diazirine (150 mg, 0.41 mmol) in methanol (5 ml) was stirred for 20 min with conc. HCl (2 drops). The solution was poured onto saturated aqueous sodium bicarbonate (10 ml) and extracted with dichloromethane (3×5 ml). The combined organic extracts were dried over sodium sulfate and evaporated under reduced pressure. The residue was taken up in dioxane (3 ml) and aqueous potassium hydroxide (2.5 ml of a 0.2M solution), potassium permanganate (98 mg, 0.62 mmol) was added and the mixture stirred for 4 h. The mixture was filtered through a pad of Celite and washed with water. The filtrate was extracted with ether (2×10 ml). The aqueous phase was brought to pH 1, extracted with ether (2×10 ml) and these extracts were dried over sodium sulfate and evaporated in vacuo to give the title compound (77 mg, 72%) as an off white solid.

PREPARATION 14

5-Amino-1,2,3,4-tetrahydroisoquinoline

A solution of 5-aminoisoquinoline (10 g, 69 mmol) in glacial acetic acid (150 ml) and concentrated sulfuric acid (1 ml) was hydrogenated over platinum oxide (1 g) at 55 psi for 20h. The acetic acid was then removed in vacuo and the residue treated with saturated aqueous potassium carbonate (100 ml) and extracted with dichloromethane. The organic layer was dried over sodium sulfate and concentrated in vacuo to afford the title compound (6.45 g).

PREPARATION 15

5-Amino-2-(tert-butoxycarbonyl)-1,2,3,4-tetrahydroisoquinoline

An ice cold solution of 5-amino-1,2,3,4-tetrahydroisoquinoline (6.45 g, 44 mmol) in 1,4-dioxane (250 ml) was treated with 3M sodium hydroxide (14.7 ml, 44 mmol), and di-tert-butyl-dicarbonate (9.57 ml, 44 mmol) and the solution was stirred at room temperature overnight. The reaction mixture was then poured into water (400 ml) and extracted with ether. The organic phases were dried over sodium sulfate and concentrated in vacuo to afford a brown oil which solidified on sthanding and was recrystallised from ethanol/petrol to afford the title compound as an off white crystalline solid (5.1 g).

PREPARATION 16

5-Chloro-2,4-dimethoxybenzoyl Chloride

A solution of 5-chloro-2,4-dimethoxybenzoic acid (6.4 g) in dichloromethane (250 ml) was treated with thionyl chloride (30 ml) and the mixture heated at reflux for 18h. Removal of volatile material in vacuo afforded the title compound as a white solid (6.6 g).

PREPARATION 17

5-Chloro-2,4-dimethoxy-N-[2-(tert-butoxycarbonyl)-1,2,3,4-tetrahydroisoquinolin-5-yl)benzamide To a solution of 5-amino-2-(tert-butoxycarbonyl)-1,2,3,4-tetrahydroisoquinoline (1 g, 4 mmol) in dichloromethane (30 ml) and triethylamine (3 ml) was added 5-chloro-2,4-dimethoxybenzoyl chloride (1.03 g, 4.4 mmol). After stirring at room temperature for 2h the reaction mixture was diluted with dichloromethane (75 ml) and washed with saturated aqueous sodium bicarbonate. The organic layer was dried over magnesium sulfate, concentrated in vacuo and the residue recrystallised from ethyl acetate/petrol to afford the title compound as a colourless crystalline solid (1.3 g).

PREPARATION 18

5-Chloro-2-methoxy-4-methylbenzoic Acid

The title compound was prepared in an analogous manner to Preparation 4 from 2-methoxy-4-methylbenzoic acid (3.0 g, 0.018 mol). Purification of the crude product using a chromatotron (SiO$_2$, 10% ethyl acetate in hexane) afforded the title compound as a white solid (0.40 g)

PREPARATION 19

5-Amino-2-ethyl-1,2,3,4-tetrahydroisoquinoline

The title compound was prepared by treatment of 5-aminoisoquinoline with iodoethane followed by reduction with sodium borohydride using procedures analogous to those described in Preparation 1 and Preparation 2.

PREPARATION 20

5-Amino-2-propyl-1,2,3,4-tetrahydroisoquinoline

The title compound was prepared by treatment of 5-aminoisoquinoline with iodopropane followed by reduction with sodium borohydride using procedures analogous to those described in Preparation 1 and Preparation 2.

PREPARATION 21

4-Benzyloxy-5-chloro-2-methoxybenzoic Acid

A solution of chlorine (5.1 g) in acetic acid (100 ml) was added dropwise to a solution of methyl 4-benzyloxy-2-methoxybenzoate (10 g) in acetic acid (40 ml) whilst maintaining the temperature at 20–25° C. The mixture was poured into ice-water and extracted with dichloromethane. The organic extract was dried over sodium sulfate and concentrated in vacuo. The resulting crude material was suspended in ethanol (500 ml) and treated with 10% aqueous sodium hydroxide (16 ml). The mixture was heated at reflux overnight and then concentrated in vacuo. The residue was treated with excess 5M HCl and extracted into dichloromethane. The extract was dried (sodium sulfate) and concentrated in vacuo to afford a white solid which was crystallised from ethanol to give the title compound (6.3 g).

PREPARATION 22

4-Hydroxy-2-methoxybenzoic Acid Methyl Ester

4-Amino-2-methoxy benzoic acid methyl ester (15 g, 82.7 mmol) was dissolved in sulfuric acid ( 80 ml of a 25% solution). The solution was cooled in an ice bath and diazotized with saturated sodium nitrite solution (8.57 g, 124 mmol) maintaining the temperature below 5° C. The diazonium solution was poured slowly into boiling sulphuric acid (1L of a 3% solution) and the mixture was heated for an additional 5 mins. The mixture was then allowed to cool before being extracted with dichloromethane. The organic extracts were combined, dried over sodium sulfate and concentrated in vacuo to afford a brown solid (9.7 g).

PREPARATION 23

4-Ethoxy-2-methoxy-benzoic Acid Methyl Ester

To a solution of 4-hydroxy-2-methoxybenzoic acid methyl ester (4.17 g, 22 mmol) in DMF (50 ml) under argon was added potassium carbonate (6.33 g, 4.6 mmol) followed by iodoethane (7.15 g, 4.6 mmol). The mixture was then heated to 50° C. under argon for 12h. On cooling the mixture was poured into a large excess of water and extracted with ether. The combined organic extracts were dried over sodium sulfate and concentrated in vacuo to afford the title compound as a brown oil (4.8 g).

PREPARATION 24

5-Chloro-4-ethoxy-2-methoxybenzoic Acid

Trifluoroacetic acid (35 ml) was cooled in an ice bath. 4-ethoxy-2-methoxy-benzoic acid methyl ester (4.85 g, 23 mmol) was then added slowly. N-chloromorpholine (3.64 g, 29.9 mmol) was then added dropwise maintaining the reaction mixture temperature below 10° C. The ice bath was removed and the mixture stirred under argon for 12h at room temperature. The solvent was then removed in vacuo and the residue taken up in ethyl acetate and washed with water. The organic layer was dried over sodium sulfate and concentrated in vacuo to afford a brown oil which was triturated with ether and 60/80 petrol. The resulting brown solid was then recrystallised from 60/80 petrol, taken up into ether and washed with sodium hydroxide solution (2M). The organic layer was dried over sodium sulfate and concentrated in vacuo to afford the methyl ester as a pale yellow solid (0.9 g). A mixture of this ester (0.9 g, 3.6 mmol), methanol (22 ml) and sodium hydroxide solution (20 ml, 2M) was heated to 70° C. overnight. On cooling the mixture was acidified to pH 6–7 and the solvent was removed in vacuo. The residue was taken up in ethanol and the inorganic solid filtered off. The filtrate was concentrated in vacuo to afford the title compound as a pale brown solid (0.44 g).

PREPARATION 25

5-Bromo-2-methoxy-4-methylbenzoic Acid

The title compound was prepared in an analogous manner to Preparation 6 from 2-methoxy-4-methylbenzoic acid (3.0 g, 0.018 mol). Recrystallisation of the crude product from dichloromethane afforded the title compound as a white solid (0.99 g).

PREPARATION 26

[4-(tert-Butyldimethylsilanyloxymethyl)-3-methoxyphenyl]-phenylmethanol

To 2-(tert-Butyldimethylsilanyloxymethyl)-5-bromoanisole (500 mg, 1.51 mmol) in THF (10 ml) at −78° C. was added n-BuLi (1.13 ml of a 1.6M solution in penthane, 1.81 mmol) and the mixture allowed to stir for 1 h at −78° C. Benzaldehyde (176 mg, 1.66 mmol) was added and the mixture allowed to warm to room temperature and stirred for 1 h. Water (20 ml) was added and the mixture extracted with ether (3×10 ml). The combined extracts were washed with water (10 ml), brine (10 ml), dried ($Na_2SO_4$) and evaporated under reduced pressure. The resulting residue was purified by chromatography ($SiO_2$, 50% ether/petrol) to give the title compound as a colourless oil (303 mg, 56%).

PREPARATION 27

[5-(tert-Butyldimethylsilanyloxymethyl)-4-methoxyphenyl]-phenylmethanol

The title compound was prepared in an analogous manner to Preparation 26 from 2-(tert-Butyldimethylsilanyloxymethyl)-4-bromoanisole (500 mg, 1.51 mmol). The crude product was purified by chromatography ($SiO_2$, 50% ether/petrol) to give the title compound as a colourless oil (63%).

PREPARATION 28

4-Benzoyl-2-methoxybenzoic Acid

A solution of 4-(tert-butyldimethylsilanyloxymethyl)-3-methoxyphenyl]-phenylmethanol (200 mg, 0.56 mmol) in THF (5 ml) was stirred with 5N HCl (5 ml) for 1 h. The mixture was poured onto saturated aqueous sodium bicarbonate (10 ml) and extracted with ether (3×10 ml). The combined organic extracts were dried ($Na_2SO_4$), and evaporated under reduced pressure. The residue was taken up in dioxane (4 ml) and aqueous KOH (5.6 ml of a 0.2M solution), potassium permanganate (266 mg, 1.68 mmol) was added and the mixture stirred for 4 h. The mixture was filtered through a pad of Celite and washed with water. The filtrate was extracted with ether (2×10 ml) and the aqueous phase was brought to pH 1 and extracted with ether (2×10 ml). These extracts were dried over sodium sulfate and evaporated in vacuo to afford the title compound as a white foam (102 mg, 71%).

PREPARATION 29

5-Benzoyl-2-methoxybenzoic Acid

The title compound was prepared in an analogous manner to Preparation 28 from [5-(tert-butyldimethylsilanyloxymethyl)-4-methoxyphenyl]-phenylmethanol (200 mg, 0.56 mmol).

The title compound was obtained as a white foam (74%).

PREPARATION 30

3-Nitro-N-methylphthalimide

A solution of 3-nitrophthalimide (Aldrich)(1.78 g, 0.01 mol) in dry N,N-dimethylformamide (20 ml) was added dropwise to a stirred suspension of sodium hydride (0.36 g of an 80% dispersion in oil; 0.012 mol) in dry N,N-dimethylformamide (10 ml) under argon. The mixture was stirred at room temperature for 30 min and then treated with iodomethane (0.75 ml, 0.012 mol). After stirring overnight the reaction was poured into ice-water and extracted with dichloromethane (4×50 ml). The combined extracts were washed with water followed by brine, then dried over sodium sulfate and concentrated in vacuo. The residue was treated with water, and the resulting precipithate was removed by filtration and washed with water. After drying in a vacuum dessicator over silica gel the title compound was obtained as a yellow solid (1.64 g).

PREPARATION 31

4-Amino-2,3-dihydro-2-methyl-1H-isoindole

A solution of 3-nitro-N-methylphthalimide (0.58 g, 2.8 mmol) in dry tetrahydrofuran (10 ml) was added dropwise to a stirred suspension of lithium aluminium hydride (0.64 g, 16.8 mmol) under argon. The mixture was stirred at room temperature for 2h and then heated under gentle reflux for 2.5h. The reaction was quenched by addition of wet diethyl ether followed by a minimum amount of water. The precipithated aluminium salts were removed by filtration. The filtrate was concentrated in vacuo to give the title compound as a brown oil (400 mg) which was used directly in the next stage (Example 31).

PREPARATION 32

6-Amino-3-methyl-2,3,4,5-tetrahydro-1H-3-benzazepine

9-Amino-6-chloro-3-methyl-2,3,4,5-tetrahydro-1H-3-benzazepine, prepared according to R. M. DeMarinis et al, J. Med. Chem., 1984, 27, 918, (0.190 g, 0.90 mmol) was dissolved in 10% acetic acid in methanol (50 ml) and 10% Pd/C (150 mg) added. The mixture was stirred at room temperature, under hydrogen/atmos pressure for 4h, then filtered through Kieselguhr and evaporated in vacuo. Residual material was taken up into dichloromethane and 5% $NaHCO_3$ solution; the organic layer was washed with brine, dried ($Na_2SO_4$) and evaporated in vacuo to afford the title compound as a colourless oil (133 mg).

PREPARATION 33

6-Amino-2-(t-butyloxycarbonyl)-1,2,3,4-tetrahydroisoquinoline

A solution of 6-amino-1,2,3,4-tetrahydroisoquinoline (0.74 g, 5 mmol) in 1,4-dioxan (50 ml) containing 5M-NaOH (1 ml) was stirred at 5° C. and treated with di-t-butyl dicarbonate (1.09 g, 5 mmol). After 20 min at room temperature the product was extracted with ethyl acetate and the material in the organic layer gave a brown gum which was chromatographed on Kieselgel 60 in 5% methanol:dichloromethane. The title compound was obtained as a pale gum (0.55 g).

$^1$H NMR ($CDCl_3$) δ: 1.49 (9H, s), 2.74 (2H, t), 3.60(4H, br), 4.46 (2H, s), 6.47 (1H, d), 6.55(1H, dd), 6.90 (1H, d).

PREPARATION 34

4-tert-Butyl-phenoxyacethate

A mixture of 3-tert-butylphenol (25.25 g, 0.1680 mole), acetic anhydride (34.31 g, 0.336 mole) and sodium acetate (13.78 g, 0.1680 mole) was heated at 100° C. for 2h. On cooling the mixture was poured into water (200 ml) and extracted with ethyl acetate (200 ml). The combined organic extracts were dried over sodium sulfate and concentrated in vacuo to afford the acetate compound as an oil (33.33 g).

PREPARATION 35

4-tert-Butyl-2-hydroxy Acetophenone

A mixture of the acethate of Preparation 34 (33.23 g, 0.173 mole) and $AlCl_3$ (25.61 g, 0.192 mole) was placed in an oil bath preheated to 120° C. and stirred mechanically. Then the oil bath temperature was raised to 165° C. and maintained for 45 min before being allowed to cool to 120° C. Then water was added dropwise into the reaction mixture (4×250 ml) to steam distil the product (bath temp 190–200° C.). The distillate was extracted with ether and the combined organic extracts were dried over sodium sulfate and concentrated in vacuo to afford 4-tert-butyl-2-hydroxy acetophenone as an oil (18.05 g).

PREPARATION 36

4-tert-Butyl-2-methoxy Acetophenone

A suspension of 4-tert-butyl-2-hydroxy acetophenone (12.65 g), potassium carbonate (13.14 g) and dimethyl sulphate (8.99 ml) in acetone (200 ml) was refluxed for 48h. After cooling, the mixture was filtered. The solvent was then removed in vacuo and the residue taken up in dichloromethane and washed with brine. The organic layer was dried over sodium sulphate and concentrated in vacuo to afford a yellow oil (12.05 g).

PREPARATION 37

4-tert-Butyl-2-methoxybenzoic Acid

The acetophenone of Preparation 36 (11.0 g, 53 mmol) was added to a solution of sodium hydroxide (28.68 g), sodium hypochlorite (182 ml, 12% w/w) and water (70 ml) at 80° C. with stirring. After heating for 1.25h, the mixture was cooled to 0° C. and a solution of sodium metabisulphite (41.1 g) in water (170 ml) was added. The mixture was stirred for 15 min and then acidified (pH1) with conc. HCl (45 ml). Work-up with ethyl acetate gave the title compound as a white solid (8.9 g).

$^1$H NMR (DMSO-$d^6$) δ: 1.30 (9H, s), 3.85(3H, s), 6.96–7.12 (2H, m), 7.60 (1H, d), 12.30–12.60 (1H, br).

PREPARATION 38

4-n-Butyl-2-methoxybenzoic Acid

A mixture of 4-bromo-2-methoxybenzoic acid methyl ester (3.0 g, 0.0122 mole), lithium chloride (1.56 g), tetra butyl tin (4.51 g) and bis (triphenyl phosphine palladium (II) chloride (214 mg, 0.3 mmol) were heated at 100° C. for 24h. The solvent was then removed in vacuo and the residue taken up in dichloromethane. The black solid was removed by filtration and the filtrate concentrated in vacuo to give a yellow oil. The oil was purified by column chromatography (Biotage) on silica gel using 10% ether in hexane to afford a colourless oil (1.63 g). A portion of the foregoing 4-n-butyl-2-methoxybenzoic acid methyl ester (1.50 g) was dissolved in methanol (35 ml) with sodium hydroxide solution (2N, 30 ml). The mixture was allowed to stir at room temperature overnight. Then added dil. HCl until pH-5. The solvent was then removed in vacuo and the residue taken up in ethyl acetate and washed with brine. The organic layer was dried over sodium sulfate and concentrated in vacuo to afford an oil (1.02 g).

PREPARATION 39

4-n-Butyl-2-methoxy-5-chlorobenzoic Acid 4-n-Butyl-2-methoxybenzoic acid (0.5 g; 2.9 mmol) and N-chloromorpholine (356 mg; 2.9 mmol) were treated in a similar manner to that described in Preparation 24 to give the title compound as a white soid (0.4 g).

PREPARATION 40

5-Bromo-4-iso-propyl-2-methoxybenzoic Acid

To a solution of 2-methoxy-4-iso-propyl benzoic acid (prepared in an analogous manner to Preparation 37, 4-tert-butyl-2-methoxy benzoic acid) (7.0 g, 36.0 mmol) in chloroform (100 ml) was added bromine (1.86 ml) in chloroform (20 ml) dropwise. The reaction was stirred at room temperature overnight. Evaporation in vacuo afforded an oil (9.27 g). $m/z$(CI): 275, 273 (MH$^+$; 70%).

PREPARATION 41

Methyl-5-bromo-4-iso-propyl-2-methoxy Benzoate

5-Bromo-4-iso-propyl-2-methoxybenzoic acid (9.268 g 34.0 mmol) was dissolved in ethanol (250 ml) and conc. H$_2$SO$_4$ (2 ml) added. The mixture was refluxed for 5h and concentrated in vacuo. Residual material was taken up into ethyl acetate and water, and the organic layer, dried (MgSO$_4$). Concentration in vacuo afforded an oil, which was purified by Biotage Column Chromatography on silica gel using 10% ether in hexane. An oil (5.5 g) was obtained.

PREPARATION 42

Methyl-4-iso-propyl-2-methoxy-5-trifluoromethyl Benzoate

A mixture of methyl-5-bromo-4-iso-propyl-2-methoxy benzoate (5.43 g, 0.0189 mole), potassium trifluoroacethate (5.75 g, 0.0378 mole) and copper (I) iodide (7.92 g, 0.042 mole) in DMF (100 ml) and toluene (30 ml) were heated at 170° C. under argon to remove water (Dean-Stark Trap) and then heated to 155° C. overnight. On cooling, after concentration in vacuo, the mixture was poured into ether (300 ml) and water (300 ml). After filtration through Kieselguhr, the organic layer was separated, washed with brine and dried (Na$_2$SO$_4$). Concentration in vacuo afforded a brown yellow solid (4.85 g).

PREPARATION 43

4-iso-Propyl-2-methoxy-5-trifluoromethyl Benzoic Acid

Methyl-4-iso-propyl-2-methoxy-5-trifluoromethyl benzoate was dissolved in methanol (100 ml), containing sodium hydroxide solution (2N, 100 ml). The mixture was allowed to stir at 25° C. overnight and then dil. HCl added until pH~5. The solvent was then removed in vacuo and the residue taken up in ethyl acetate and washed with brine. The organic layer was dried over sodium sulfate and concentrated in vacuo to afford a crude solid which as recrystallised with dichloromethane and hexane to give a solid (2.59 g).

PREPARATION 44

5-Pivaloyl-2-methoxy Benzoic Acid

5-Pivaloyl-2-methoxy benzyl alcohol (1.19 g, 5.35 mmol) was dissolved in dioxane (20 ml). A solution of KOH (0.449 g, 8.025 mmol in water (5 ml) was added followed by KMnO$_4$ (1.69 g, 10.7 mmol). The mixture was allowed to stir at room temperature over the weekend. The solution was filtered through Celite and extracted with ether. The aqueous phase was acidified with dil. HCl and extracted with ether (3×50 ml). The organic layer was dried over magnesium sulphate and concentrated in vacuo to afford the title compound as a white solid (1.06 g).

PREPARATION 45

5-Pivaloyl-2-methoxy Benzyl Alcohol

5-Pivaloyl-2-methoxy benzyl TBDMS ether (1.8 g, 5.35 mmol) was dissolved in methanol (30 ml); conc. HCl (20 drops) was added and the whole allowed to stir at room temperature for 4h. Saturated NaHCO$_3$ solution was added and the mixture extracted with ether (2×100 ml). The organic layer was dried over sodium sulfate and concentrated in vacuo to afford the title compound as a colourless oil (1.19 g).

PREPARATION 46

5-Pivaloyl-2-methoxy Benzyl TBDMS Ether n-Butyllithium (11.43 ml, 0.0183 mole, 1.6M in hexane) was slowly added to a solution of 5-bromo-2-methoxy benzyl TBDMS ether in tetrahydrofuran (30 ml) over 45 mins at −31 78° C. The reaction mixture was maintained under argon at −78° C. for 1h. Then N,O-dimethylhydroxy dimethylhydroxy pivaloyl amide (2.43 g, 0.0167 mole) was added dropwise with stirring at −78° C. The resulting mixture was allowed to stir at −78° C. for 2.5h, quenched with NH$_4$Cl solution and allowed to warm to room temperature. The mixture was extracted with ether (2×50 ml), the combined organics were dried (Na$_2$SO$_4$) and concentrated in vacuo to give an oil. The oil was purified by Biotage column chromatography on silica gel using 5% ether in hexane to afford the title compound as a colourless oil (2.95 g).

PREPARATION 47

5-Bromo-2-methoxy Benzyl TBMS Ether

To a solution of 5-bromo-2-methoxy benzyl alcohol (20.87 g, 0.096 mole) in dichloromethane (300 ml), Et$_3$N (20.90 ml, 0.15 mole) was added tert-butyldimethylsilyl chloride (15.94 g, 0.10 mole) dropwise. The mixture was allowed to stir at room temperature overnight, then water (300 ml) was added. The organic layer was washed with brine, dried (Na$_2$SO$_4$) and evaporated to give a white solid. The title compound was purified by dry flash column chromatography on silica gel using 20% ether in hexane to give a white solid (20.1 g).

PREPARATION 48

2,4-Dimethoxy-5-trifluoromethylbenzoic Acid 2,4-Dimethoxy-5-bromobenzoic acid methyl ester (1.5 g; 5.4 mmol) in DMF (25 ml) and toluene (8 ml) under argon was treated with potassium trifluoroacethate (1.53 g; 10.1 mmol) and copper (I) iodide (2.1 g, 10.9 mmol). The mixture was heated to 170° C. with removal of water (Dean/Stark), and then at 155° C. overnight. The mixture was allowed to cool, poured into ether and water and filtered through Kieselguhr. The organic layer was dried (Na$_2$SO$_4$) and concentrated in vacuo to give a brown solid. Chromatography on Kieselgel 60 with 1:1 ether/petrol gave a white solid (1.03 g) which was hydrolised in 1:1 methanolic: aqueous NaOH (50 ml) at 50° C. Work-up gave the title compound as a white solid (1 g).

PREPARATION 49

2-Methoxy-4-(3-trifluoromethyl-3H-diazirinyl) benzoic Acid

The title compound was prepared from 4-bromo-2-methoxybenzyl alcohol using a method similar to that described in Preparations 7 to 13.

PREPARATION 50

5-Iodo-2-methoxy-4-(3-trifluoromethyl-3H-diazirinyl)benzoic Acid

The benzoic acid of Preparation 49 (100 mg) in triflic acid (2 ml) containing N-iodosuccinimide (104 mg) was stirred at room temperature overnight. The mixture was poured onto ice/water and extracted into ether. The combined organic extracts were washed with aqueous sodium thiosulfate, dried (MgSO$_4$) and evaporation in vacuo gave the title compound as an off-white solid (115 mg; 78%).

PREPARATION 51

N-2-(4-Nitrophenyl)ethyl-trifluoroacetamide

A solution of trifluoroacetic anhydride (10.6 ml) in dichloromethane (100 ml) was added dropwise to a stirred solution of 2,6- lutidine (17.44 ml) and 4-nitrophenethylamine hydrochloride (15.2 g; 75 mmol) at 0° C. The mixture was stirred at 25° C. overnight under argon and then washed with dilute citric acid (×2), brine and dried over Na$_2$SO$_4$. The material in the organic phase gave the title compound as a pale yellow solid (19.04 g).

PREPARATION 52

7-Nitro-1,2,3,4-tetrahydro-2-trifluoroacetyl-isoquinoline

The nitro compound of Preparation 51 (2.26 g; 9.15 mmol) and paraformaldehyde (0.45 g; 14.4 mmol) in acetic acid (10 ml) and conc. H$_2$SO$_4$ (15 ml) were stirred at 25° C. for 20h according to the procedure of G. E. Stokker., Tet. Lett., 1996, 37, 5453. Work up afforded the title compound as a white solid (2.17 g).

$^1$H NMR (CDCl$_3$) δ: 3.10 (2H, m), 3.92 (2H, m), 4.85+ 4.92 (2H, 2×s), 7.38 (1H, t), 8.10 (2H, m). $^m/_z$(EI): 274 (M$^+$)

PREPARATION 53

7-Nitro-1,2,3,4-tetrahydroisoquinoline

The trifluoroacetamide of Preparation 52 (17.22 g; 63 mmol) was hydrolysed at room temperature using a solution of potassium carbonate (46.6 g) in 10% aqueous methanol (660 ml). Work-up with dichloromethane gave the title compound (11 g).

PREPARATION 54

2-Methyl-7-nitro-1,2,3,4-tetrahydroisoquinoline

The amine of Preparation 53 (2.08 g; 11.7 mmol) was treated with 88% formic acid (3.45 ml) and 37% aqueous formaldehyde (5.88 ml) at 80° C. for 2h according to the procedure of G. M. Carrera and D. S. Garvey, J. Het. Chem., 1992, 29, 847. Basification with 10% sodium hydroxide followed by work-up with ethyl acetate afforded an orange gum(2.3 g). Chromatography on Kiesegel 60 in 0–3% methanol-ethyl acetate gave the title compound as an orange solid (1.7 g).

$^m/_z$(CI): 193 (MH$^+$)

PREPARATION 55

7-Amino-2-methyl-1,2,3,4-tetrahydroisoquinoline

The 7-nitro compound of Preparation 54 (0.25 g; 1.3 mmol) in methanol (40 ml) was hydrogenated over 10% palladium on carbon (100 mg) at atmospheric pressure overnight. The catalyst was removed by filtration through a pad of Kieselguhr and evaporation in vacuo gave the title compound as a white solid (213 mg).

$^m/_z$(CI): 163 (MH$^+$)

PREPARATION 56

7-Amino-2-(t-butyloxycarbonyl)-1,2,3,4-tetrahydroisoquinoline

The title compound was prepared from the compound of Preparation 53 using di t-butyl dicarbonate in 10% aqueous hydroxide in dioxan at 25° C. followed by catalytic hydrogenation according to the procedures described for Preparations 15 and 55.

PREPARATION 57

7-Amino-1,2,3,4-tetrahydro-2-trifluoroacetyl-isoquinoline

The 7-nitro compound of Preparation 52 (0.99 g; 3.6 mmol) in ethanol (50 ml) was hydrogenated over 10% palladium on carbon (450 mg) at atmospheric pressure for 4h. The catalyst was removed by filtration through a pad of Celite and evaporation in vacuo gave the title compound as a white solid (840 mg).

$^1$H NMR (250 MHz, CDCl$_3$) δ: 2.84 (2H, t), 3.23 (2H, br s), 3.82 (2H, m), 4.66 (2H,d, restricted rothation around C-1), 6.47 (1H, m), 6.57 (1H,m ), 6.96 (1H, m)

PREPARATION 58

2-Methyl-5-nitro-1,2,3,4-tetrahydroisoquinoline

5-Nitroisoquinoline was quaternized with methyl iodide and then reduced using sodium borohydride according to the procedures of Preparations 1 and 2 to give the title compound.

PREPARATION 59

7-Iodo-2-methyl-5-nitro-1,2,3,4-tetrahydroisoquinoline

The nitro compound of Preparation 58 (100 mg; 0.52 mmol) and N-iodosuccinimide (118 mg) in triflic acid (3 ml) was stirred at 25° C. overnight. The mixture was poured cautiously into saturated NaHCO$_3$ and then extracted into ether (2×). The combined organic extracts were washed with aqueous sodium thiosulfate, dried (MgSO$_4$) and evaporation in vacuo gave a residue. Chromatography on Kieselgel 60 in 1% methanol-dichloromethane gave the title compound (101 mg; 61%).

$^m/_z$(API$^+$): 319 (MH$^+$; 100%).

PREPARATION 60

5-Amino-7-iodo-2-methyl-1,2,3,4-tetrahydroisoquinoline

A solution of the nitro compound of Preparation 59 (101 mg) in ethanol (20 ml) at 50° C. was treated with a solution of tin (II) chloride (243 mg) in conc. hydrochloric acid (1 ml). The resultant yellow solution was basified with 10% aqueous sodium hydroxide and the product extracted into dichloromethane. Flash chromatography on Kieselgel 60 (5% methanol-dichloromethane) gave the title compound (65 mg; 70%).

$^1$H NMR (CDCl$_3$) δ: 2.40 (3H, s), 2.46 (2H, t), 2.68 (2H, t), 2.90–3.50 (2H, br), 3.42 (2H, s), 6.75(1H, d, J=1.5 Hz), 6.81 (1H, d, J=1.5 Hz). $^m/_z$(API): 289(MH$^+$; 100%).

PREPARATION 61

7-Amino-5-iodo-2-trifluoroacetyl-1,2,3,4-tetrahydroisoquinoline

The title compound was prepared from the nitro compound of Preparation 52 using a procedure similar to that of Preparations 59 and 60.

PREPARATION 62

5-Amino-7-iodo-2-trifluoroacetyl-1,2,3,4-tetrahydroisoquinoline

The title compound was prepared from 5-nitro-1,2,3,4-tetrahydroisoquinoline using procedures similar to those outlined in Preparations 51, 59 and 60.

PREPARATION 63

8-Fluoro-1,2,3,4-tetrahydroisoquinoline

The title compound was prepared using a method similar to that described by W. L. Mendelson et al; Tethrahedron Lett., 1980, 21, 1393.

PREPARATION 64

5-Nitro-8-fluoro-2-methyl-1,2,3,4-tetrahydroisoquinoline

The compound of Preparation 63 was nitrated using potassium nitrate and conc. sulfuric acid using sthandard conditions to give 5-nitro-8-fluoro-1,2,3,4-tetrahydroisoquinoline. This was treated with 88% formic acid and 37% aqueous formaldehyde at 80° C. for 2h according to the procedure of G. M. Carrera and D. S. Garvey, J. Het. Chem., 1992, 29, 847 to give the title compound.

PREPARATION 65

5-Amino-8-fluoro-2-methyl-1,2,3,4-tetrahydroisoquinoline

The title compound was prepared by hydrogenation of 5-nitro-8-fluoro-2-methyl-1,2,3,4-tetrahydroisoquinoline (Preparation 64) using a method similar to that of Preparation 55 with ethyl acetate as solvent.

$m/z(API^+)$: 181 ($MH^+$; 80%)

EXAMPLE 1

N-(2-Methyl-1,2,3,4-tetrahydroisoquinolin-5-yl)-4-amino-5-chloro-2-methoxy-benzamide Hydrochloride 4-Amino-5-chloro-2-methoxybenzoic acid (2.08 g, 11.1 mmol), 1-(3-dimethylaminopropyl)-3-ethylcarbodiimide hydrochloride (1.77 g 9.24 mmol) and 1-hydroxybenzotriazole (1.25 g, 9.24 mmol) were dissolved in dry DMF (40 ml) and stirred at room temperature under argon for 0.5h before 5-amino-2-methyl-1,2,3,4-tetrahydroisoquinoline (1.5 g, 9.24 mmol) was added. The mixture was then stirred for 18 h under argon at room temperature. The DMF was removed in vacuo and the residue taken up into ethyl acetate and washed with water, saturated aqueous sodium bicarbonate and brine. The organic layer was dried over sodium sulfate and concentrated in vacuo to afford a yellow solid. This was then passed through a short pad of silica eluting with dichloromethane to afford a white solid which was then taken up into methanol and treated with hydrogen chloride (1M in ether, 1 equivalent). The solvent was removed in vacuo and the residue recrystallised from methanol and ethyl acetate to afford the title compound as a white solid (0.775 g).

$^1$H NMR(DMSO-d6) δ: 2.93 (3H, s), 3.10 (2H, s), 3.30 (2H, s), 3.90 (3H, s), 4.30–4.50 (2H, brs), 6.10 (2H, s), 6.60 (1H, s), 6.97 (1H, d, J=6 Hz), 7.28 (1H, t, J=6 Hz), 7.80 (1H, s), 8.00 (1H, d, J=6 Hz), 9.63 (1H, s), 10.89 (1H, s).

EXAMPLE 2

N-(2-Methyl-1,2,3,4-tetrahydroisoquinolin-5-yl)-2,4-dimethoxybenzamide Hydrochloride To a solution of 5-amino-2-methyl-1,2,3,4-tetrahydroisoquinoline (0.25 g, 1.54 mmol) in ethyl acethate (5 ml) was added 2,4-dimethoxybenzoyl chloride (0.263 g 1.54 mmol). The mixture was stirred under argon for 2 h before the precipithate was filtered off and dried to afford the title compound as white solid.

$^1$H NMR (DMSO-d6) δ: 2.90 (3H, s), 3.05(2H, br. s), 3.35(2H, s),3.85(3H, s), 4.03 (3H, s), 4.25–4.55(2H, m), 6.70 (1H, dd, J's=1,6 Hz), 6.75(1H, m), 7.00 (1H, d, J=6 Hz), 7.30 (1H, t, J=6 Hz), 7.95(2H, m), 9.75(1H, s), 11.25 (1H, br. s); m/z (M+H)+327.

EXAMPLE 3

N-(2-Methyl-1,2,3,4-tetrahydroisoquinolin-5-yl)-2-methoxybenzamide Hydrochloride The title compound was prepared in an analogous fashion to Example 2 from 5-amino-2-methyl-1,2,3,4-tetrahydroisoquinoline and 2-methoxybenzoyl chloride.

$^1$H NMR (DMSO-d6) δ: 2.90 (3H, s), 3.08 (2H, m), 3.38 (1H, m), 3.75(1H, m), 4.00 (3H, s), 4.30 (1H, m), 4.50 (1H, m), 7.05(1H, d, J=8 Hz), 7.11 (1H, t, J=8 Hz), 7.23 (1H, d, J=8 Hz), 7.31 (1H, t, J=8 Hz), 7.55(1H, t, J=8 Hz), 7.85(2H, m), 9.85(1H, s), 10.95(1H, br, s); m/z (M+H)+297.

EXAMPLE 4

N-(2-Methyl-1,2,3,4-tetrahydroisoquinolin-5-yl)-5-chloro-2-methoxybenzamide

The title compound was prepared in an analogous manner to Example 1 from 5-amino-2-methyl-1,2,3,4-tetrahydroisoquinoline and 5-chloro-2-methoxybenzoic acid.

$^1$H NMR (DMSO-d6) δ: 2.36 (3H, s), 2.67 (2H, m), 2.73 (2H, m), 3.51 (2H, s), 3.98 (3H, s), 6.92 (1H, d, J=6 Hz), 7.16 (1H, t, J=7 Hz), 7.28 (1H, d, J=8 Hz), 7.61 (1H, dd, J's=3,10 Hz), 7.71 (1H, d, J=8 Hz), 7.83 (1H, d, J=3 Hz), 9.79 (1H, s); m/z (M+H)+331.

EXAMPLE 5

N-(2-Methyl-1,2,3,4-tetrahydroisoquinolin-5-yl)-4-chloro-2-methoxybenzamide

The title compound was prepared in an analogous manner to Example 1 from 5-amino-2-methyl-1,2,3,4-tetrahydroisoquinoline and 4-chloro-2-methoxybenzoic acid.

$^1$H NMR (DMSO-d6) δ: 2.40 (3H, s), 2.78 (4H, br. s), 3.60 (2H, br. s), 4.02 (3H, s), 6.93 (1H, d, J=5 Hz), 7.18 (1H, dd, J's=1,5 Hz), 7.35(1H, d, J=1 Hz), 7.74 (1H,d, J=5 Hz), 7.89 (1H, d, J=5 Hz), 9.71 (1H, s); m/z (M+H)+331.

EXAMPLE 6

N-(2-Methyl-1,2,3,4-tetrahydroisoquinolin-5-yl)-4-acetylamino-5-bromo-2-methoxybenzamide The title compound was prepared in an analogous manner to Example 1 from 5-amino-2-methyl-1,2,3,4-tetrahydroisoquinoline and 4-acetylamino-5-bromo-2-methoxybenzoic acid.

$^1$H NMR (DMSO-d6) δ: 2.15(3H, s), 2.35(3H, s), 2.61–2.81 (4H, m), 3.50 (2H, m) 3.98 (3H, s), 6.90 (1H, d, J=6 Hz), 7.15(1H, t, J=6 Hz), 7.72 (1H, s) 7.78 (1H, d, J=8 Hz), 8.07 (1H, s), 9.22 (1H, s), 9.53 (1H, s); m/z (M+H)+432.

EXAMPLE 7

N-(2-Methyl-1,2,3,4-tetrahydroisoquinolin-5-yl)-4-amino-5-bromo-2-methoxybenzamide To a solution of 4-acetylamino-5-bromo-2-methoxy-N-(2-methyl-1,2,3,4-tetrahydroisoquinolin-5-yl)benzamide (0.888 g, 2 mmol) in ethanol (30 ml) and water (10 ml) was added 10% aqueous sodium hydroxide (1.25 ml). The mixture was heated at reflux for 1.25h before pouring into water and extracting with chloroform. The organic layer was dried over sodium sulfate, concentrated in vacuo and the residue recrystallised from ethyl acethate to afford the title compound as a brown solid (0.062 g).

$^1$H NMR (DMSO-d6) δ: 2.34 (3H, s), 2.68 (4H, m), 3.45(2H, s), 3.95(3H, s), 6.08 (2H, s), 6.57 (1H, s), 6.80 (1H, d, J=6 Hz), 7.12 (1H, t, J=6 Hz), 7.95(1H, d, J=6 Hz), 7.99 (1H, s), 9.60 (1H, s); m/z (M+H)+390.

EXAMPLE 8

N-(2-Methyl-1,2,3,4-tetrahydroisoquinol-5-yl)-4-azido-5-iodo-2-methoxybenzamide

The title compound was prepared in an analogous manner to Example 1 from 5-amino-2-methyl-1,2,3,4-tetrahydroisoquinoline and 4-azido-5-iodo-2-methoxybenzoic acid.

$^1$H NMR (CDCl3) δ: 2.48 (3H, s), 2.75–2.85(4H, m), 3.62 (2H, s), 4.10 (3H, s), 6.74 (1H, s), 6.87 (1H, d, J=7 Hz), 7.22 (1H, t, J=7 Hz), 8.08 (1H, d, J=7 Hz), 8.69 (1H, s), 9.50 (1H, br. s); m/z (M+H)+464.

EXAMPLE 9

N-(2-Methyl-1,2,3,4-tetrahydroiso quinolin-5-yl)-4-acetylamino-5-chloro-2-propoxy-benzamide The title compound was prepared in an analogous manner to Example 1 from 5-amino-2-methyl-1,2,3,4-tetrahydroisoquinoline and 4-acetylamino-5-chloro-2-propoxybenzoic acid.

$^1$H NMR (DMSO-d6) δ: 0.96 (3H, t, J=6 Hz), 1.84 (2H, m), 2.18 (3H, s), 2.37 (3H, s), 2.65(2H, m), 2.75(2H, m), 3.53 (2H, s), 4.14 (2H, t, J=6 Hz), 6.92 (1H, d, J=6 Hz), 7.15(1H, t, J=6 Hz), 7.65(1H, d, J=6 Hz), 7.85(1H, s), 7.90 (1H, s), 9.58 (1H, s), 9.64 (1H, s); m/z (M+H)+416.

EXAMPLE 10

N-(2-Methyl-1,2,3,4-tetrahydroisoquinolin-5-yl)-4-amino-5-chloro-2-propoxy-benzamide 4-Acethylamino-5-chloro-2-propoxy-N-(2-methyl-1,2,3, 4-tetrahydroisoquinolin-5-yl)benzamide (0.877 g, 2 mmol) was added to a mixture of 10% sodium hydroxide (1.25 ml) and water (5 ml) in ethanol (30 ml) and heated at reflux for 1.25h. The mixture was then cooled, poured into a large volume of water and extracted with chloroform. The organic layer was dried over sodium sulfate, concentrated in vacuo and the residue recrystallised from ethyl acethate to afford the title compound as a yellow crystalline solid (387 mg).

$^1$H NMR (DMSO-d6) δ: 0.98 (3H, t, J=6 Hz), 1.85(2H, m), 2.35(3H, s), 2.64 (2H, m), 2.70 (2H, m), 3.50 (2H, s), 4.15(2H, t, J=6 Hz), 6.10 (2H, s), 6.60 (1H, s), 6.85(1H, d, J=6 Hz), 7.12 (1H, t, J=6 Hz), 7.80 (1H, s), 7.96 (1H, s), 9.42 (1H, s); m/z (M+H)+374.

EXAMPLE 11

N-(2-Methyl-1,2,3,4-tetrahydroisoquinolin-5-yl)-4-acetylamino-2-methoxybenzamide The title compound was prepared in an analogous manner to Example 1 from 5-amino-2-methyl-1,2,3,4-tetrahydroisoquinoline and 4-acetylamino-2-methoxybenzoic acid.

$^1$H NMR(DMSO-d6) δ: 2.08 (3H, s), 2.52 (3H, s), 2.87 (4H, br. s), 3.71 (2H, br.s), 3.99 (3H, s), 6.90 (1H, d, J=8 Hz), 7.17 (1H, t, J=7 Hz), 7.35(1H, d, J=8 Hz), 7.70 (1H, s), 7.91 (2H, m), 9.75(1H, s), 10.71 (1H, s); m/z (M+H)+354.

EXAMPLE 12

N-(2-Methyl-1,2,3,4-tetrahydroisoquinolin-5-yl)-5-chloro-2-methoxy-4-nitrobenzamide The title compound was prepared in an analogous manner to Example 1 from 5-amino-2-methyl-1,2,3,4-tetrahydroisoquinoline and 5-chloro-2-methoxy-4-nitrobenzoic acid.

$^1$H NMR (DMSO-d6) δ: 2.35(3H, s), 2.63 (2H, m), 2.77 (2H, m), 3.51 (2H, s), 3.99 (3H, s), 6.99 (1H, d, J=5 Hz), 7.17 (1H, t, J=5 Hz), 7.54 (1H, d, J=5 Hz), 7.91 (1H,s), 7.99 (1H, s), 9.77 (1H, s); m/z (M+H)+376.

EXAMPLE 13

N-(2-Methyl-1,2,3,4-tetrahydroisoquinolin-5-yl)-4-amino-5-iodo-2-methoxybenzamide The title compound was prepared in an analogous manner to Example 1 from 5-amino-2-methyl-1,2,3,4-tetrahydroisoquinoline and 4-amino-5-iodo-2-methoxybenzoic acid.

$^1$H NMR (DMSO-d6) δ: 2.35(3H, s), 2.70 (4H, m), 3.50 (2H, s), 3.95(3H, s), 5.95 (2H, s), 6.55(1H, s), 6.82 (1H, d, J=6 Hz), 7.13 (1H, t, J=6 Hz), 7.95(1H, d, J=6 Hz), 8.18 (1H, s), 9.58 (1H, s); m/z (M+H)+438.

EXAMPLE 14

N-(2-Methyl-1,2,3,4-tetrahydroisoquinolin-5-yl)-4-benzyloxy-5-chloro-2-methoxybenzamide The title compound was prepared in an analogous manner to Example 1 from 5-amino-2-methyl-1,2,3,4-tetrahydroisoquinoline and 4-benzyloxy-5-chloro-2-methoxybenzoic acid.

$^1$H NMR (DMSO-d6) δ: 2.35(3H, s), 2.68 (2H, m), 2.76 (2H, m), 3.49 (2H, s), 4.08 (3H, s), 5.39 (2H, s), 6.88 (1H, d, J=7 Hz), 7.09 (1H, s), 7.16 (1H, t, J=7 Hz), 7.37–7.57 (5H, m), 7.85(1H, d, J=7 Hz), 7.95(1H, s), 9.68 (1H, s); m/z (M+H)+437.

EXAMPLE 15

N-(2-Methyl-1,2,3,4-tetrahydroisoquinolin-5-yl)-4,5-dichloro-2-methoxybenzamide

The title compound was prepared in an analogous manner to Example 1 from 5-amino-2-methyl-1,2,3,4-tetrahydroisoquinoline and 4,5-dichloro-2-methoxybenzoic acid $^1$H NMR (DMSO-d6) δ: 2.34 (3H, s), 2.65(2H, m), 2.76 (2H, m), 3.50 (2H, s), 4.03 (3H, s), 6.92 (1H, d, J=7 Hz), 7.16 (1H, t, J=7 Hz), 7.55(1H, s), 7.67 (1H, d, J=8 Hz), 7.98 (1H, s), 9.70 (1H, s); m/z (M+H)+365.

EXAMPLE 16

N-(2-Methyl-1,2;3,4-tetrahydroisoquinolin-5-yl)-5-chloro-2,4-dimethoxybenzamide

5-Chloro-2,4-dimethoxybenzoic acid (0.245 g, 1.1 mmol), 1-(3-dimethyl aminopropyl)-3-ethylcarbodiimide hydrochloride (0.186 g, 0.94 mmol) and 1-hydroxybenzotriazole (0.144 g, 0.94 mmol) were dissolved in dry DMF (10 ml) and stirred at room temperature under argon for 25 mins before 5-amino-2-methyl-1,2,3,4-tetrahydroisoquinoline (0.153 g, 0.94 mmol) was added. The mixture was then stirred for 24h under argon at room temperature. The DMF was removed in vacuo and the residue taken up into ethyl acetate and washed with water. The organic layer was dried over magnesium sulfate, concentrated in vacuo and the residue recrystallised from ethyl acetate/hexane to afford the title compound as a solid (0.069 g).

$^1$H NMR (DMSO-d6) δ: 2.34 (3H, s), 2.67 (2H, m), 2.75(2H, m), 3.49 (2H, s), 3.99 (3H, s), 4.10 (3H, s), 6.87 (1H, d, J=5 Hz), 6.95(1H, s) 7.15(1H, t, J=5 Hz), 7.89 (1H, d, J=5 Hz), 7.94 (1H, s), 9.70 (1H, s); m/z (M+H)+361.

EXAMPLE 17

N-(2-Methyl-1,2,3,4-tetrahydroisoquinolin-5-yl)-5-bromo-2,4-dimethoxybenzamide

5-Bromo-2,4-dimethoxybenzoic acid (0.296 g, 1.1 mmol), 1-(3-dimethyl aminopropyl)-3-ethylcarbodiimide hydrochloride (0.186 g, 0.94 mmol) and 1-hydroxybenzotriazole (0.144 g, 0.94 mmol) were dissolved in dry DMF (10 ml) and stirred at room temperature under argon for 25 mins before 5-amino-2-methyl-1,2,3,4-tetrahydroisoquinoline (0.153 g, 0.94 mmol) was added. The mixture was then stirred overnight under argon at room temperature. The DMF was removed in vacuo and the residue taken up into ethyl acetate and washed with water. The organic layer was dried over magnesium sulfate, concentrated in vacuo and the residue recrystallised from ethyl acetate/hexane to afford the title compound as a solid (0.106 g)

$^1$H NMR (DMSO-d6) δ: 2.35(3H, s), 2.68 (2H, m), 2.75(2H, d, m), 3.49 (2H, s), 3.99 (3H, s), 4.12 (3H, s), 6.89 (2H, m), 7.15(1H, t, J=7 Hz), 7.85(1H, d, J=7 Hz), 8.09 (1H, s), 9.68 (1H, s); m/z (M+H)+405.

EXAMPLE 18

N-(2-Methyl-1,2,3,4-tetrahydroisoquinol-5-yl)-5-[3-(trifluoromethyl)-3H-diazirin-3-yl]-2-methoxybenzamide The title compound was prepared in an analogous manner to Example 1 from 5-amino-2-methyl-1,2,3,4-tetrahydroisoquinoline and 5-[3-(trifluoromethyl)-3H-diazirin-3-yl]-2-methoxybenzoic acid.

$^1$H NMR, (CDCl$_3$) δ: 2.40 (3H, s), 2.65–2.78 (4H, m), 3.54 (2H, s), 4.00 (3H, s), 6.80 (1H, d, J=7 Hz), 7.02 (1H, d, J=7 Hz), 7.14 (1H, t, J=7 Hz), 7.36 (1H, dd, J's=2,7 Hz), 7.98–8.12 (2H, m), 9.50 (1H, s); m/z (M+H)+405.

EXAMPLE 19

N-(1,2,3,4-Tetrahydroisoquinolin-5-yl)-5-chloro-2,4-dimethoxybenzamide

To a solution of 5-chloro-2,4-dimethoxy-N-[2-(tert-butoxycarbonyl)-1,2,3,4-tetrahydroisoquinolin-5-yl] benzamide (1 g) in dichloromethane (30 ml) at 0° C. was added trifluoracetic acid (3 ml). The mixture was then stirred at room temperature for 3h before pouring into saturated aqueous sodium bicarbonate (100 ml) and extracting with dichloromethane. The organic phase was dried over sodium sulfate and concentrated in vacuo to afford the title compound as an off white solid (700 mg).

$^1$H NMR (DMSO-d6) δ: 2.62 (2H, m), 3.06 (2H, m), 3.85(2H, s), 4.00 (3H, s), 4.10 (3H, s), 6.86 (1H, d, J=7 Hz), 6.96 (1H, s), 7.13 (1H, t, J=7 Hz), 7.86 (1H, d, J=7 Hz), 7.94 (1H, s), 9.70 (1H, s); m/z (M+H)+347.

EXAMPLE 20

N-(2-Methyl-1,2,3,4-tetrahydroisoquinolin-5-yl)-5-chloro-2-methoxy-4-methylbenzamide 5-Chloro-2-methoxy-4-methylbenzoic acid (0.202 g, 1 mmol), 1-(3-dimethyl aminopropyl)-3-ethylcarbodiimide hydrochloride (0.200 g, 1 mmol) and 1-hydroxy-benzotriazole (0.155 g, 25 mmol) were dissolved in dry DMF (10 ml) and stirred at room temperature under argon for 25 mins before 5-amino-2-methyl-1,2,3,4-tetrahydroisoquinoline (0.163 g, 1 mmol) was added. The mixture was then stirred for 24 under argon at room temperature. The DMF was removed in vacuo and the residue suspended in ethyl acetate and washed with water. The insoluble white precipithate was filtered off, washed with water then dried to afford the title compound (149 mg).

$^1$H NMR (methanol-d4) δ: 2.48 (3H, s), 3.07 (3H, s), 3.16 (2H, m), 3.63 (2H, m), 4.09 (3H, s), 4.46 (2H, s), 7.13 (1H, d, J=9 Hz), 7.22 (1H, s), 7.38 (1H, t, J=9 Hz), 7.78 (1H, d, J=9 Hz), 7.98 (1H, s); m/z (M+H)+345.

EXAMPLE 21

N-(2-n-Propyl-1,2;3,4-tetrahydroisoquinolin-5-yl)-5-chloro-2,4-dimethoxybenzamide Hydrochloride The title compound was prepared in an analogous manner to Example 2 from 5-amino-2-n-5propyl-1,2,3,4-tetrahydroisoquinoline and 5-chloro-2,4-dimethoxybenzoyl chloride.

$^1$H NMR (DMSO-d6) δ: 0.95(3H, t, J=7 Hz), 1.82 (2H, m), 3.10 (3H, m), 3.35(1H, m), 3.50 (1H, m), 3.77 (1H, m), 4.00 (3H, s), 4.11 (3H, s), 4.34 (1H, m), 4.54 (1H, m), 6.95(1H, s), 7.05(1H, d, J=6 Hz), 7.32 (1H, t, J=6 Hz), 7.89 (2H, m), 9.75(1H, s), 10.93 (1H, br. s); m/z (M+H)+389.

EXAMPLE 22

N-(2-Ethyl-1,2,3,4-tetrahydroisoquinolin-5-yl)-5-chloro-2,4-dimethoxybenzamide Hydrochloride The title compound was prepared in an analogous manner to Example 2 from 5-amino-2-ethyl-1,2,3,4-tetrahydroisoquinoline and 5-chloro-2,4-dimethoxybenzoyl chloride.

$^1$H NMR (DMSO-d6) δ: 1.36 (3H, t, J=7 Hz), 3.09 (2H, m), 3.12–3.85(4H, m), 4.00 (3H, s), 4.10 (3H, s), 4.30 (1H, m), 4.55(1H, m), 6.94 (1H, s), 7.06 (1H, d, J=6 Hz), 7.32 (1H, t, J=6 Hz), 7.89 (2H, m), 9.76 (1H, s), 10.85(1H, br.s); m/z (M+H)+375.

EXAMPLE 23

N-(2-Methyl-1,2,3,4-tetrahydroisoquinolin-5-yl)-5-chloro-4-ethoxy-2-methoxybenzamide The title compound was prepared in an analogous manner to Example 1 from 5-amino-2-methyl-1,2,3,4-tetrahydroisoquinoline and 5-chloro-4-ethoxy-2-methoxybenzoic acid.

$^1$H NMR (DMSO-d6) δ: 1.42 (3H, t, J=6 Hz), 2.34 (3H, s), 2.70 (4H, m), 3.50 (2H, s), 4.08 (3H, s), 4.28 (2H, m), 6.87 ( 1H, d, J=6 Hz), 6.93 (1H, s), 7.15(1H, the J=6 Hz), 7.86 (1H, d, J=6 Hz), 7.94 (1H, s), 9.70 (1H, s); m/z (M=H)+375.

EXAMPLE 24

N-(2-Methyl-1,2,3,4-tetrahydroisoquinolin-5-yl)-2,5-dimethoxybenzamide

The title compound was prepared in an analogous manner to Example 1 from 5-amino-2-methyl-1,2,3,4-tetrahydroisoquinoline and 2,5-dimethoxybenzoic acid.

$^1$H NMR (DMSO-d6) δ: 2.94 (2H, m), 3.04 (3H, s), 3.34 (2H, m), 3.58 (2H, m), 3.77 (3H, s), 3.95(3H, s), 7.16 (2H, m), 7.35(1H, m), 7.40 (1H, d, J=4 Hz), 7.75(1H, d, J=9 Hz), 7.92 (1H, d, J=9 Hz), 10.00 (1H, s); m/z (M+H)+327.

EXAMPLE 25

N-(2-Methyl-1,2,3,4-tetrahydroisoquinolin-5-yl)-5-bromo-2-methoxy-4-methylbenzamide 5-Bromo-2-methoxy-4-methylbenzoic acid (0.245 g, 1 mmol), 1-(3-dimethyl-aminopropyl)-3-ethylcarbodiimide hydrochloride (0.200 g, 1 mmol) and 1-hydroxy-benzotriazole (0.155 g, 1 mmol) were dissolved in dry DMF (10 ml) and stirred at room temperature under argon for 25 mins before 5-amino-2-methyl-1,2,3,4-tetrahydroisoquinoline (0.163 g, 1 mmol) was added. The mixture was then stirred for 24 under argon at room temperature. The DMF was removed in vacuo and the residue suspended in ethyl acetate and washed with water. The insoluble white precipithate was filtered off, washed with water then dried to afford the title compound (210 mg).

$^1$H NMR (methanol-d4) δ: 2.49 (3H, s), 3.05(2H, m), 3.07 (3H, s), 3.15(2H, m), 3.62 (2H, m), 4.08 (3H, s), 4.47 (2H, s), 7.13 (1H, d, J=8 Hz), 7.22 (1H, s), 7.38 (1H, t, J=7 Hz), 7.77 (1H, d, J=8 Hz), 8.14 (1H, s); m/z (M+H)+389

EXAMPLE 26

N-(2-Methyl-1,2,3,4-tetrahydroisoquinolin-5-yl)-5-dimethylsulfamoyl-2-methoxybenzamide The title compound was prepared in an analogous manner to Example 1 from 5-amino-2-methyl-1,2,3,4-tetrahydroisoquinoline and 5-dimethylsulfamoyl-2-methoxybenzoic acid.

$^1$H NMR (DMSO-d6) δ: 2.36 (3H, s), 2.60 (6H, s), 2.65(2H, m), 2.79 (2H, m), 3.51 (2H, s), 4.08 (3H, s), 6.92 (1H, d, J=7 Hz), 7.17 (1H, t, J=7 Hz), 7.48 (1H, d, J=7 Hz), 7.79 (1H, d, J=7 Hz), 7.90 (1H, dd, J's=1,7 Hz), 8.15(1H, d, J=1 Hz), 9.74 (1H, s); m/z (M+H)+404.

EXAMPLE 27

N-(2-Methyl-1,2,3,4-tetrahydroisoquinolin-5-yl)-4-benzoyl-2-methoxybenzamide The title compound was prepared in an analogous manner to Example 1 from 5-amino-2-methyl-1,2,3,4-tetrahydroisoquinoline and 4-benzoyl-2-methoxybenzoic acid.

$^1$H NMR (CDCl$_3$) δ: 2.6 (3H, s), 2.70–2.87 (4H, m), 3.54 (2H, s), 4.06 (3H, s), 6.70 (1H, d, J=7 Hz), 7.23 (1H, d, J=7 Hz), 7.62-7.30 (5H, m), 7.68–7.83 (2H, m), 8.10 (1H, d, J=7 Hz), 8.32 (1H, d, J=7 Hz), 9.7 (1H, br s); m/z (M+H)+401.

EXAMPLE 28

N-(2-Methyl-1,2,3,4-tetrahydroisoquinolin-5-yl)-5-benzoyl-2-methoxybenzamide The title compound was prepared in an analogous manner to Example 1 from 5-amino-2-methyl-1,2,3,4-tetrahydroisoquinoline and 5-benzoyl-2-methoxy-benzoic acid.

$^1$H NMR (CDCl$_3$) δ: 2.50 (3H, s), 2.72–2.92(4H, m), 3.63 (2H, s), 4.16 (3H, s), 6.87 (1H, d, J=7 Hz), 7.15–7.26 (2H, m), 7.45–7.65(3H, m), 7,76–7.85(2H, m), 8.08–8.19 (2H, m), 8.75(1H, d, J=2 Hz), 9.60 (1H, br s); m/z (M+H)+401.

EXAMPLE 29

N-(2-Methyl-1,2,3,4-tetrahydroisoquinolin-8-yl)-4-acetylamino-5-chloro-2-methoxybenzamide To a cooled solution of 4-acetylamino-5-chloro-2-methoxybenzoyl chloride, (prepared from 4-acetylamino-5-chloro-2-methoxybenzoic acid, 3.19 g) in dichloromethane was added 8-amino-2-methyl-1,2,3,4-tetrahydroisoquinoline (2.1 g) and triethylamine (4 ml). After stirring at room temperature for 2.5h, the mixture was basified with 10% sodium hydroxide. The organic layer was separated, dried and concentrated in vacuo. The residue was purified by chromatography on alumina eluting with chloroform, and then crystallised from ethyl acethate to give the title compound.

EXAMPLE 30

N-(2-Methyl-1,2,3,4-tetrahydroisoquinolin-8-yl)-4-amino-5-chloro-2-metboxybenzamide To a solution of 4-acetylamino-5-chloro-2-methoxy-N-(2-methyl-1,2,3,4-tetrahydroisoquinolin-8-yl)benzamide (0.95 g) in ethanol (20 ml) and water (10 ml) was added sodium hydroxide (0.1 g) and the mixture was heated on a steam bath for 45 min. The reaction was concentrated in vacuo and the residue partitioned between methylene chloride and water. The organic phase was dried and concentrated in vacuo. Purification by chromatography on alumina eluting with chloroform followed by crystallisation from ethyl acethate afforded the title compound (0.51 g) m.p.= 192–193° C.

$^1$H NMR δ: 2.50 (3H, s), 2.50–2.99 (4H, m), 3.51 (2H, s), 3.95(3H, s), 4.48 (2H, br s), 6.31 (1H, s), 6.86–7.27 (2H, m), 7.90–8.00 (1H, m), 8.17 (1H, s), 9.30 (1H, br s).

EXAMPLE 31

N-(2,3-Dihydro-2-methyl-1H-isoindol-4-yl)-5-chloro-2,4-dimethoxybenzamide Hydrochloride A solution of freshly prepared 4-amino-2,3-dihydro-2-methyl-1H-isoindole (400 mg, 3.0 mmol) in dry ethyl acetate (40 ml) under argon was treated dropwise with a solution of 5-chloro-2,4-dimethoxybenzoyl chloride (700 mg, 3.0 mmol) in a mixture of ethyl acetate (10 ml) and dichloromethane (10 ml). The reaction was stirred at room temperature for 6h and then concentrated in vacuo. The residue was triturated with diethyl ether/ethyl acetate and then crystallised twice from methanol/diethyl ether to give the title compound as a pale grey solid (0.11 g).

$^1$H NMR (DMSO-d6) δ: 3.01 (3H, s), 4.02 (3H, s), 4.06 (3H, s), 4.4–4.8 (4H, br m), 6.93 (1H, s), 7.26 (1H, d, J=8 Hz), 7.42 (1H, t, J=8 Hz), 7.56 (1H, d, J=8 Hz), 7.82 (1H, s), 9.98 (1H, s), 11.88 (1H, br s); m/z (M+H)+347.

EXAMPLE 32

N-(3-Methyl-2,3,4,5-tetrahydro-1H-3-benzazepine-6-yl)-4-tert-butyl-2-methoxybenzamide, Hydrochloride The title compound was prepared from 6-amino-3-methyl-2,3,4,5-tetradydro-1H-3-benzazepine and 4-tert-butyl-2-methoxybenzoic acid.

¹H NMR (DMSO-d⁶) δ: 1.32 (9H, s), 2.79 (3H, s), 3.08 (5H, m), 3.33 (1H, m), 3.60 (2H, m), 3.96 (3H, s), 7.28 (5H, m), 7.65(1H, d, J=10 Hz), 9.84 (1H, s), 10.82 (1H, br s). $m/z$(CI): 367 (MH⁺)

EXAMPLE 33

N-(1,2,3,4-Tetrahydroisoquinolin-6-yl)-4-t-butyl-2-methoxybenzamide, Trifluoroacethate The title compound was prepared from amine Preparation 33 (190 mg; 0.77 mmol) and 4-t-butyl-2-methoxybenzoic acid (174 mg; 0.84 mmol) according to the procedure of Example 1. The product (350 mg) in dichloromethane (20 ml) containing trifluoroacetic acid (1 ml) was kept at 25° C. for 18 hr and evaporation in vacuo followed by crystallisation of the residue from ethyl acetate:ether gave the title compound as off-white crystals (295 mg), m.p. 207–211° C.

¹H NMR (DMSO-d⁶) δ: 1.33 (9H, s), 3.00 (2H, t), 3.39 (2H, t), 3.94 (3H, s), 4.25(2H, s), 7.10 (2H, m), 7.18 (1H, d), 7.55(1H, dd), 7.60 (1H, d), 7.69 (1H, s), 9.03 (2H, br), 10.05(1H, s); Found: M⁺338.1998 calc for $C_{21}H_{26}N_2O_2$ 338.2010

EXAMPLE 34

N-(2-Methyl-1,2,3,4-tetrahydroisoquinolin-6-yl)-4-t-butyl-2-methoxybenzamide, Trifluoroacethate The compound of Example 33 (168 mg; 0.37 mmol) and paraformaldehyde (224 mg; 7.4 mmol) in dry tetrahydrofuran (5 ml) was stirred at 25° C. under argon and treated with sodium borohydride (152 mg; 4 mmol) and trifluoroacetic acid (2 ml) according to the procedure of G. W. Gribble, Synthesis 1987, 709. Work-up gave a yellow gum (62 mg).

¹H NMR (CDCl₃) δ: 1.36 (9H, s), 2.50 (3H, s), 2.75(2H, t), 2.97 (2H, t), 3.63 (2H, s), 4.06 (3H, s), 7.00 (2H, d), 7.16 (1H, dd), 7.35(1H, dd), 7.56 (1H, br s), 8.20 (1H, d), 9.76 (1H, s).

Treatment with trifluoroacetic acid followed by crystallisation from ethyl acetate:ether gave the title compound as white crystals (64 mg), m.p. 205–8° C.; Found: M⁺352.21549 Calc for $C_{22}H_{28}N_2O_2$ 352.21666.

EXAMPLE 35

N-(2-Methyl-1,2,3,4-tetrahydroisoquinolin-5-yl)-4-tert-butyl-2-methoxybenzamide Hydrochloride The title compound was prepared in an analogous manner to Example 1 from 5-amino-2-methyl-1,2,3,4-tetrahydroisoquinoline and 4-tert-butyl-2-methoxybenzoic acid.

¹H NMR (DMSO-d⁶) δ: 1.32 (9H, s), 2.91 (3H, s), 3.06 (2H, m), 3.35(1H, m), 3.70 (1H, m), 4.02 (3H, s), 4.45(2H, m), 7.04 (1H, d, J=10 Hz), 7.15(2H, m), 7.31 (1H, m), 7.82 (1H, d, J=12 Hz), 7.90 (1H, d, J=12 Hz), 9.83 (1H, s), 10.82 (1H, s). $m/z$CI: 353 (MH⁺).

EXAMPLE 36

N-(2-Methyl-1,2,3,4-tetrahydroisoquinolin-5-yl)-4-n-butyl-2-methoxy-5-chloro-benzamide, Hydrochloride The title compound was prepared in a similar manner to Example 1 from 5-amino-2-methyl-1,2,3,4-tetrahydroisoquinoline and 4-n-butyl-2-methoxy-5-chlorobenzoic acid.

¹H NMR (DMSO-d⁶) δ: 0.93 (3H, m), 1.38 (2H, m), 1.58 (2H, m), 2.63 (2H, m), 2.90 (3H, s), 3.07 (2H, m), 3.35(1H, m), 3.70 (1H, m), 4.00 (3H, s), 4.34 (1H, m), 4.48 (1H, m), 7.06 (1H, d, J=12 Hz), 7.23 (1H, s), 7.33 (1H, m), 7.80 (2H, m), 9.83 (1H, s), 11.90 (1H, br s). $m/z$(CI): 387 (MH⁺)

EXAMPLE 37

N-(2-Methyl-1,2,3,4-tetrahydroisoquinolin-5-yl)-4-ethyl-2-methoxy-5-chloro Benzamide, Hydrochloride The title compound was prepared in an analogous manner to Example 1 from 5-amino-2-methyl-1,2,3,4-tetrahydroisoquinoline and 4-ethyl-2-methoxy-5-chlorobenzoic acid.

¹H NMR (DMSO d⁶)δ: 1.24 (3H, m), 2.77 (2H, m), 2.91 (3H, s), 3.15(2H, m), 3.35(1H, m), 3.65(1H, m), 4.02 (3H, s), 4.40 (2H, m), 7.07 (1H, d, J=9 Hz), 7.26 (1H, s), 7.34 (1H, m), 7.77 (2H, m), 9.85(1H, s), 10.72 (1H, br s) $m/z$(CI): 359 (MH⁺).

EXAMPLE 38

N-(2-Methyl-1,2,3,4-tetrahydroisoquinolin-5-yl)-4-tert-butyl-2-methoxy-5-chloro-benzamide, Hydrochloride The title compound was prepared in an analogous manner to Example 1 from 5-amino-2-methyl-1,2,3,4-tetrahydroisoquinoline and 4-tert-butyl-2-methoxy-5-chlorobenzoic acid.

¹H NMR (DMSO-d⁶) δ: 1.49 (9H, s), 2.91 (3H, s), 3.05(2H, m), 3.18 (2H, s), 3.35(1H, m), 4.03 (3H, s), 4.42 (1H, m), 7.08 (1H, d, J=8 Hz), 7.20 (1H, s), 7.33 (1H, m), 7.79 (2H, m), 9.82 (1H, s), 10.66 (1H, br s). $m/z$(CI): 387 (MH⁺, 90%)

EXAMPLE 39

N-(2-Methyl-1,2,3,4-tetrahydroisoquinolin-5-yl)-2-methoxy-4-phenylbenzamide, Hydrochloride The title compound was prepared in an analogous manner to Example 1 from 5-amino-2-methyl-1,2,3,4-tetrahydoisoquinoline and 2-methoxy-4-phenylbenzoic acid.

¹H NMR (DMSO-d⁶)δ: 2.94 (3H, d), 3.11 (2H, m), 3.40 (1H, m), 3.78 (1H, m), 4.14 (3H, s), 4.35(1H, m), 4.55(1H, m), 7.08 (1H, d, J=9 Hz), 7.35(1H, m), 7.50 (5H, m), 7.81 (2H, m), 7.89 (1H, d), 7.99 (1H, m), 9.92 (1H, s), 10.80 (1H, br s). $m/z$(CI): 373 (MH⁺, 100%).

EXAMPLE 40

N-(1,2,3,4-Tetrahydroisoquinolin-5-yl)-4-tert-butyl-2-methoxybenzamide Hydrochloride The title compound was prepared in an analogous manner to Example 19.

¹H NMR (DMSO-d⁶)δ: 1.31 (9H, s), 2.97 (2H, m), 3.37 (2H, m), 3.44 (2H, m), 4.06 (3H, s), 4.31 (2H, m), 7.08 (1H, d, J=9 Hz), 7.16 (2H, m), 7.28 (1H, m), 7.84 (2H, m), 9.55(2H, br s), 9.83 (1H, s). $m/z$(CI): 339 (MH⁺; 80%).

EXAMPLE 41

N-(2-Methyl-1,2,3,4-tetrahydroisoquinolin-5yl)-4-iso-propyl-2-methoxybenzamide, Hydrochloride The title compound was prepared in an analogous manner to Example 1 from 5-amino-2-methyl-1,2,3,4-tetrahydroisoquinoline and 4-iso-propyl-2-methoxybenzoic acid.

¹H NMR (DMSO-d⁶)δ: 1.26 (6H, d), 2.92 (3H, s), 2.99 (1H, m), 3.09 (1H, m), 3.39 (1H, m), 3.73 (1H, m), 4.02 (3H, s), 4.33 (1H, m), 4.50 (1H, m), 7.03 (2H, m), 7.10 (1H, s), 7.31 (1H, m), 7.83 (2H, m), 9.83 (1H, s), 10.97 (1H, br s). $m/z$(CI): 339 (MH⁺).

EXAMPLE 42

N-(2-Methyl-1,2,3,4-tetrahydroisoquinolin-5-yl)-5-chloro-4-iso-propyl-2-methoxybenzamide, hydrochloride The title compound was prepared in an analogous manner to Example 1 from 5-amino-2-methyl-1,2,3,4-tetrahydroisoquinoline and 5-chloro-4-iso-propyl-2-methoxybenzoic acid.

¹H NMR (DMSO-d⁶) δ: 1.28 (6H, d), 2.91 (3H, m), 3.07 (2H, m), 3.33 (1H, m), 3.70 (1H, m), 4.03 (3H, s), 4.30 (1H, m), 4.52 (1H, m), 7.06 (1H, d, J=9 Hz), 7.16 (1H, s), 7.32 (1H, m), 7.76 (2H, m), 9.86 (1H, s), 10.68 (1H, br s). $m/z$(CI): 373 (MH⁺; 90%).

EXAMPLE 43

N-(1,2,3,4-Tetrahydroisoquinolin-5-yl)-5-chloro-4-tert-butyl-2-methoxybenzamide, Hydrochloride The title compound was prepared in an analogous manner to Examples 19, 20.

¹H NMR (DMSO-d⁶) δ: 1.50 (9H, s), 2.95(2H, m), 3.42 (2H, m), 4.05(3H, s), 4.30 (2H, m), 7.10 (1H, d), 7.20 (1H, s), 7.30 (1H, m), 7.76 (2H, m), 9.50 (2H, br s), 9.81 (1H, s). $m/z$(CI): 373 (MH+; 100%)

EXAMPLE 44

N-(2-Methyl-1,2,3,4-tetrahydroisoquinolin-5-yl)-4-ethyl-2-methoxybenzamide, Hydrochloride The title compound was prepared in an analogous manner to Example 1 from 5-amino-2-methyl-1,2,3,4-tetrahydroisoquinoline and 4-ethyl-2-methoxybenzoic acid.

¹H NMR (DMSO-d⁶) δ: 1.23 (3H, t), 2.68 (2H, q), 2.91 (3H, s), 3.06 (2H, m), 3.35(1H, m), 3.71 (1H, m), 4.00 (3H, s), 4.40 (2H, m), 7.0 (2H, m), 7.10 (1H, s), 7.30 (1H, m), 7.87 (2H, m), 9.80 (1H, s), 10.83 (1H, s). $m/z$(CI): 325(MH⁺; 100%).

EXAMPLE 45

N-(2-Methyl-1,2,3,4-tetrahydroisoquinolin-5-yl)-5-bromo-4-iso-propoxy-2-methoxybenzamide, Hydrochloride ¹H NMR (DMSO-d⁶) δ: 1.36 (6H, d), 2.92 (3H, m), 3.05(2H, m), 3.49 (1H, m), 3.77 (1H, m), 4.06 (3H, s), 4.33 (1H, m), 4.55(1H, m), 4.93 (1H, m), 6.91 (1H, s), 7.05(1H, d), J=9 Hz), 7.31 (1H, m), 7.84 (1H, d, J=10 Hz), 8.02 (1H, s), 9.76 (1H, s), 10.57 (1H, br s). $m/z$(CI): 435(MH⁺)

EXAMPLE 46

N-(2-Methyl-1,2,3,4-tetrahydroisoquinolin-5-yl)-4-iso-propyl-5-trifluoromethyl-2-methoxybenzamide, Hydrochloride ¹H NMR (DMSO-d⁶) δ: 1.30 (6H, d), 2.90 (3H, s), 3.05(2H, m), 3.30 (1H, m), 3.50 (2H, m), 4.07 (3H, s), 4.39 (2H, m), 7.06 (1H, d, J=9 Hz), 7.31 (2H, m), 7.74 (1H, d, J=10 Hz), 8.02 (1H, s), 9.86 (1H, s), 11.00 (1H, br s). $m/z$(CI): 407 (MH⁺; 90%).

EXAMPLE 47

N-(2-Methyl-1,2,3,4-tetrahydroisoquinolin-5-yl)-4-iso-propoxy-2-methoxy-5-trifluoromethyl-benzamide, Hydrochloride ¹H NMR (DMSO-d⁶) δ: 1.33 (6H, d), 2.91 (3H, s), 3.06 (2H, m), 3.35(1H, m), 3.69 (1H, m), 4.11 (3H, s), 4.40 (2H, m), 5.06 (1H, m), 7.04 (2H, m), 7.31 (1H, m), 7.82 (1H, d, J=10 Hz), 8.10 (1H, s), 9.75(1H, s), 11.00 (1H, br s). $m/z$(CI): 423 (MH⁺; 100%).

EXAMPLE 48

N-(2-Methyl-1,2,3,4-tetrahydroisoquinolin-5-yl)-5-bromo-4-iso-propyl-2-methoxybenzamide, Hydrochloride ¹H NMR (DMSO-d⁶)δ: 1.22 (6H, d), 2.90 (3H, s), 3.06 (2H, m), 3.33 (3H, m), 4.03 (3H, s), 4.43 (2H, m), 7.05(1H, d, J=8 Hz), 7.17 (1H, s), 7.31 (1H, m), 7.70 (1H, d, J=10 Hz), 7.94 (1H, s), 9.82 (1H, s), 10.94 (1H, br s). $m/z$(CI): 419 (MH⁺)

EXAMPLE 49

N-(2-Methyl-1,2,3,4-tetrahydroisoquinolin-5-yl) 5-iso-butyroyl-2-methoxy-benzamide Hydrochloride The title compound was prepared in a similar manner to that of Example 50.

¹H NMR (DMSO-d⁶)δ: 1.06 (6H, d), 2.84 (3H, s), 3.04 (2H, m), 3.31 (1H, m), 3.62 (2H, m), 3.97 (3H, s), 4.37 (2H, m), 7.02 (1H, d, J=10 Hz), 7.30 (2H, m), 7.66 (1H, d, J=10 Hz), 8.12 (1H, dd, J=12, 3 Hz), 8.30 (1H, d, J=3.3 Hz), 9.80 (1H, s), 10.91 (1H, br s). $m/z$(CI): 367 (MH⁺)

EXAMPLE 50

N-(2-Methyl-1,2,3,4-tetrahydroisoquinolin-5-yl)-5-pivaloyl-2-methoxybenzamide, Hydrochloride The title compound was prepared in an analogous manner to Example 1 from 5-amino-2-methyl-1,2,3,4-tetrahydroisoquinoline and 5-pivaloyl-2-methoxy benzoic acid.

¹H NMR (DMSO-d⁶)δ: 1.40 (9H, s), 2.95(3H, s), 3.13 (2H, m), 3.35(2H, m), 4.10 (3H, s), 4.47 (2H, m), 7.14 (1H, d, J=10 Hz), 7.39 (2H, m), 7.80 (1H, d, J=10 Hz), 8.14 (1H, d, J=12 Hz), 8.54 (1H, s), 9.93 (1H, s), 10.65(1H, br s). $m/z$(CI): 381 (MH⁺)

EXAMPLE 51

N-(2-Methyl-1,2,3,4-tetrahydroisoquinolin-7-yl)-5-chloro-2-methoxy-4-iso-propoxybenzamide, Trifluoroacethate m.p. 164–9° C.

Free base: ¹H NMR (CDCl₃)δ: 1.44 (6H, d), 2.46 (3H, s), 2.70 (2H, t), 2.91 (2H, t), 3.60 (2H, s), 4.04 (3H, s), 4.66 (1H, m), 6.56 (1H, s), 7.08 (1H, d), 7.28 (1H, dd), 7.46 (1H, d), 8.27 (1H, s), 9.53 (1H, s). $m/z$(CI): 389 (MH⁺; 50%).

EXAMPLE 52

N-(2-Methyl-1,2,3,4-tetrahydroisoquinolin-7-yl)-5-bromo-2,4-dimethoxybenzamide, Hydrochloride Salt ¹H NMR (250 MHz, CDCl₃+CD₃OD) δ: 2.89–3.19(4H, m and overlapping s at 2.98 and HOD signal), 3.27 (1H, m), 3.46 (1H, m, overlapping with CHD$_2$OD signal), 3.70 (1H, m), 4.00 (3H, s), 4.11 (4H, overlapping s and d), 4.58 (1H, br d), 6.54 (1H, s), 7.18 (1H, d), 7.38 (1H, d), 7.61 (1H, br s), 8.36 (1H, s), 9.69 (partially exchanged 1H, br s).

EXAMPLE 53

N-(2-Methyl-1,2,3,4-tetrahydroisoquinolin-7-yl)-4-tert-butyl-2-methoxybenzamide $^1$H NMR (250 MHz, CDCl$_3$) δ: 1.35(9H, s), 2.46 (3H, s), 2.68 (2H, t), 2.89 (2H, s), 3.59 (2H, s), 4.06 (3H, s), 7.01 (1H, d), 7.07 (1H, d), 7.15(1H, dd), 7.31 (1H, dd), 7.50 (1H, d), 8.19 (1H, d), 9.74 (1H, br s)

EXAMPLE 54

N-(2-Methyl-1,2,3,4-tetrahydroisoquinolin-7-yl)-2-methoxy-4-methyl-5-trifluoromethylbenzamide $^1$H NMR (250 MHz, CDCl$_3$) δ: 2.47 (3H, s), 2.54 (3H, s), 2.70 (2H, t), 2.91 (2H, t), 3.60 (2H, s), 4.10 (3H, s), 6.91 (1H, s), 7.09 (1H, d), 7.30 (1H, dd), 7.48 (1H, d), 8.54 (1H, s), 9.55(1H, br s).

EXAMPLE 55

N-(2-Methyl-1,2,3,4-tetrahydroisoquinolin-7-yl)-2-methoxybenzamide, Hydrochloride Salt $^1$H NMR (250 MHz, CD$_3$OD)δ: 3.00–3.53 (6H, m and overlapping s at 3.07 and CHD$_2$OD signal), 3.69–3.86 (1H, br m), 4.02 (3H, s), 4.36.(1H, d), 4.57 (1H, d), 7.10 (1H, t), 7.20 (1H, d), 7.28 (1H, d), 7.48–7.60 (2H, overlapping signals), 7.73 (1H, s), 7.88 (1H, dd).

EXAMPLE 56

N-(2-Methyl-1,2,3,4-tetrahydroisoquinolin-7-yl)-2,4-dimethoxybenzamide, Hydrochloride Salt $^1$H NMR (200 MHz, CD$_3$OD)δ: 2.90–3.60 (6H, m overlapping with s at 3.09 and CHD$_2$OD signal), 3.60–3.95(4H, m overlapping with s at 3.91), 4.08 (3H, s), 4.38 (1H, d), 4.60 (1H, d), 6.67–6.78 (2H, m, overlapping signals), 7.30 (1H, d), 7.53 (1H, dd), 7.73 (1H, s), 7.99 (1H, d).

EXAMPLE 57

N-(2-Methyl-1,2,3,4-tetrahydroisoquinolin-7-yl)-5-chloro-2-methoxybenzamide $^1$H NMR (250 MHz, CDCl$_3$)δ: 2.46 (3H, s), 2.69 (2H, t), 2.89 (2H, t), 3.60 (2H, s), 4.04 (3H, s), 6.97 (1H, d), 7.09 (1H, d), 7.30 (1H, dd), 7.39–7.49 (2H, m, overlapping signals), 8.24 (1H, d), 9.65(1H, br s).

EXAMPLE 58

N-(2-Methyl-1,2,3,4-tetrahydroisoquinolin-5-yl)-4-iso-propoxy-2-methoxybenzamide, Hydrochloride $^1$H NMR (DMSO-d$^6$) δ: 1.31 (6H, d, J=7 Hz), 3.42 (3H, s), 3.04 (2H, m), 3.29–3.78 (2H, br m), 4.02 (3H, s), 4.24–4.56 (2H, m), 4.78 (1H, m), 6.35(1H, m), 6.70 (2H, m), 7.02 (1H, m), 7.32 (1H, t, J=6 Hz), 7.95(2H, m), 9.73 (1H, s), 10.83 (1H, br s). $^m/_z$(CI): 355(MH$^+$)

EXAMPLE 59

N-(2-Methyl-1,2,3,4-tetrahydroisoquinolin-5-yl)-5-dimethylsulfamoyl-2,4-dimethoxybenzamide, Hydrochloride $^1$H NMR (DMSO-d$^6$)δ: 2.72 (6H, s), 2.91 (2H, m), 3.05(2H, m), 3.38 (1H, m), 3.72 (1H, m), 4.05(3H, s), 4.15(3H, s), 4.35(1H, m), 4.56 (1H, m), 7.95(1H, s), 7.06 (1H, d, J=6 Hz), 7.33 (1H, t, J=6 Hz), 7.80 (1H, d, J=6 Hz), 8.28 (1H, s), 9.72 (1H, s), 10.82 (1H, s).

EXAMPLE 60

N-(2-Methyl-1,2,3,4-tetrahydroisoquinolin-5-yl)-2-methoxy-5-iso-propylsulfonylbenzamide, Hydrochloride $^1$H NMR (DMSO d$^6$)δ: 1.18 (6H, d, J=6 Hz), 2.90 (3H, s), 3.11 (2H, m), 3.25–3.42 (2H, m), 3.70 (1H, m), 4.06 (3H, s), 4.34 (1H, m), 4.51 (1H, m), 7.08 (1H, d, J=6 Hz), 7.34 (1H, d, J=6 Hz), 7.47 (1H, d, J=6 Hz), 8.00 (1H, d, J=6 Hz), 8.15(1H, s), 9.95(1H, s), 11.22 (1H, br s). $^m/_z$(CI): 403 (MH$^+$)

EXAMPLE 61

N-(2-Methyl-1,2,3,4-tetrahydroisoquinolin-5-yl)-5-chloro-2-methoxy-4-phenylbenzamide, Hydrochloride $^1$H NMR (DMSO-d$^6$)δ: 2.93 (3H, d), 3.10 (2H, br m), 3.35(1H, br m), 3.70 (1H, br, overlapped), 4.04 (3H, s), 4.33 (1H, dd), 4.55(1H, d), 7.10 (1H, d), 7.25(1H, s), 7.36 (1H, t), 7.55(5H, br s), 7.78 (1H, d), 7.93 (1H, s). $^m/_z$(CI): 407 (MH$^+$, 100%).

EXAMPLE 62

N-(1,2,3,4-Tetrahydroisoquinolin-5-yl)-5-bromo-2,4-dimethoxybenzamide, Trifluoroacethate $^1$H NMR (400 MHz, CDCl$_3$+MeOH-d$^4$) δ: 2.99 (2H, t, overlapping HOD), 3.48 (2H, t), 4.00 (3H, s), 4.11 (3H, s), 4.34 (2H, s), 6.58 (1H, s), 7.02 (1H, d), 7.27–7.36 (1H, m, overlapping CHCl$_3$), 7.75(1H, d), 8.38 (1H, s).

EXAMPLE 63

N-(2-Methyl-1,2,3,4-tetrahydroisoquinolin-5-yl)-2-methoxy-5-n-propylsulfonylbenzamide, Hydrochloride $^1$H NMR (DMSO-d$^6$)δ: 0.92 (3H, t, J=8 Hz), 1.56 (2H, m), 2.90 (3H, s), 3.09 (2H, m), 3.36 (3H, m), 3.73 (1H, m), 4.02 (3H, s), 4.33 (1H, m), 4.52 (1H, m), 7.09 (1H, d, J=7 Hz), 7.32 (1H, t, J=7 Hz), 7.47 (1H, d, J =8 Hz), 7.67 (1H, d, J=8 Hz), 8.03 (.H, dd, J=7, 1 Hz), 8.20 (1H, d, J=1 Hz), 9.92 (1H, s), 11.0 (1H, br s). $^m/_z$(CI): 403 (MH$^+$).

EXAMPLE 64

N-(2-Methyl-1,2,3,4-tetrahydroisoquinolin-5-yl)-2,4-dimethoxy-5-trifluoromethylbenzamide, Hydrochloride $^1$H NMR (DMSO-d$^6$)δ: 2.41 (3H, s), 3.04 (2H, m), 3.30–3.78 (2H, m), 4.03 (3H, s), 4.13 (3H, s), 4.40 (2H, m), 7.05(2H, m), 7.32 (1H, t, J=6 Hz), 7.85(1H, d, J=6 Hz), 8.12 (1H, s), 9.72 (1H, s), 11.32 (1H, br s). $^m/_z$(CI): 395(MH$^+$)

EXAMPLE 65

N-(2-Methyl-1,2,3,4-tetrahydroisoquinolin-5-yl)-2-methoxy-4-methyl-5-trifluoromethylbenzamide, Hydrochloride $^1$H NMR (DMSO-d$^6$)δ: 2.94 (3H, s), 3.08 (2H, m), 3.42 (1H, m), 3.70 (1H, m), 4.06 (3H, s), 4.40 (2H, m), 7.09 (1H, d, J=6 Hz), 7.34 (2H, m), 7.75(1H, d, J=6 Hz), 8.08 (1H, s), 9.82 (1H, s), 10.83 (1H, s). $^m/_z$(CI): 379 (MH$^+$)

EXAMPLE 66

N-(2-Methyl-1,2,3,4-tetrahydroisoquinolin-5-yl)-5-acetyl-2,4-dimethoxybenzamide, Hydrochloride $^1$H NMR (DMSO-d$^6$)δ: 2.48 (3H, s); 2.58 (3H, s), 2.92 (2H, m), 3.02 (2H, m), 3.38 (2H, m), 4.06 (3H, s), 4.12 (3H, s), 7.06 (1H, d, J=8 Hz), 7.33 (.H, t, J=8 Hz), 7.78 (1H, d, J=8 Hz), 8.28 (1H, s), 9.70 (1H, s). $^m/_z$(CI): 369 (MH$^+$; 100%).

EXAMPLE 67

N-(2-Methyl-1,2,3,4-tetrahydroisoquinolin-5-yl)-5-bromo-4-ethyl-2-methoxybenzamide, Hydrochloride $^1$H NMR (DMSO-d$^6$)δ: 1.21 (3H, t, J=8 Hz), 2.50 (3H, s), 2.78 (2H, q, J=8 Hz), 2.92 (4H, m), 3.05(2H, m), 4.00 (3H, s), 7.06 (1H, d, J=7 Hz), 7.25(1H, s), 7.32 (1H, t, J=7 Hz), 7.74 (1H, d, J=7 Hz), 7.93 (1H, s), 9.82 (1H, s), 10.40 (1H, br s). $^m/_z$(CI): 405, 403 (MH$^+$, 100%).

EXAMPLE 68

N-(2-Methyl-1,2,3,4-tetrahydroisoquinolin-5-yl)-4-ethyl-2-methoxy-5-trifluoromethylbenzamide, Hydrochloride $^1$H NMR (DMSO-d$^6$)δ: 1.40 (3H, t, J=8 Hz), 2.94 (2H, m), 2.99 (3H, s), 3.17 (2H, m), 3.45(3H, s), 3.75(1H, m), 4.11 (1H, m), 4.24 (3H, s), 4.50 (2H, m), 7.17 (1H, d, J=7 Hz), 7.42 (2H, m), 7.86 (1H, d, J=7 Hz), 8.16 (1H, s), 9.94 (1H, s), 11.26 (1H, br s) $^m/_z$(CI): 393 (MH$^+$)

EXAMPLE 69

N-(2-Methyl-1,2,3,4-tetrahydroisoquinolin-5-yl)-4-n-butoxy-5-chloro-2-methoxybenzamide, Hydrochloride $^1$H NMR (DMSO-d$^6$)δ: 0.98 (3H, t, J=6 Hz), 1.48 (2H, m), 1.29 (2H, m), 2.89 (3H, s), 3.06 (2H, m), 3.70 (1H, m), 4.10 (3H, s), 4.24 (2H, t, J=6 Hz), 4.48 (1H, m), 6.95(1H, s), 7.04 (1H, d, J=6 Hz), 7.32 (1H, t, J=6 Hz), 7.79 (2H, m), 9.75(1H, s), 11.20 (1H, br s). $^m/_z$(CI): 403 (MH$^+$)

EXAMPLE 70

N-(2-Methyl-1,2,3,4-tetrahydroisoquinolin-5-yl)-2-methoxy-4-iso-propyloxy-5-acetyl-benzamide, Hydrochloride $^1$H NMR (free base; CDCl$_3$) δ: 1.39 (6H, d, J=7 Hz), 2.48 (3H, s), 2.59 (3H, s), 2.79 (4H, m), 3.61 (2H, s), 4.09 (3H, s), 4.76 (1H, s), 6.51 (1H, s), 6.84 (1H, d, J=8 Hz), 7.20 (1H, t, J=8 Hz), 8.13 (1H, d, J=8 Hz), 8.73 (1H, s), 9.36 (1H, br s). $^m/_z$(CI): 397 (MH$^+$; 100%).

EXAMPLE 71

N-(2-Methyl-1,2,3,4-tetrahydroisoquinolin-5-yl)-5-chloro-2-methoxy-4-iso-propoxybenzamide, Hydrochloride $^1$H NMR (DMSO d$^6$)δ: 1.37 (6H, d, J=6 Hz), 2.92 (3H, s), 3.05(2H, m), 3.37 (1H, m), 3.73 (1H, m), 4.08 (3H, s), 4.32 (1H, m), 4.51 (1H, m), 4.96 (1H, m), 6.95(1H, s), 7.06 (1H, d, J=6 Hz), 7.32 (1H, t, J=6 Hz), 7.89 (2H, m), 9.27 (1H, s), 11.20 (1H, br s). $^m/_z$(CI): 389 (MH$^+$, 80%)

EXAMPLE 72

N-(2-Methyl-1,2,3,4-tetrahydroisoquinolin-5-yl)-2-methoxy-5-iodo-4-trifluoromethyldiazirinyl Benzamide $^1$H NMR (200 MHz, CDCl$_3$)δ: 2.48 (3H, s), 2.81 (4H, br s), 3.64 (2H, br s), 4.13 (3H, s), 6.88 (1H, d), 7.20 (1H, t), 7.23 (1H, s), 8.05(1H, d), 8.77 (1H, s), 9.50 (1H, br s). $^m/_z$(CI): 531 (MH$^+$)

EXAMPLE 73

N-(1,2,3,4-Tetrahydroisoquinolin-5-yl)-4-azido-5-iodo-2-methoxybenzamide, Trifluoroacethate $^1$H NMR (200 MHz, MeOD-d$^4$)δ: 3.13 (2H, t), 3.53 (2H, t), 4.14 (3H, s), 4.38 (2H, s), 6.89 (1H, s), 7.12 (1H, d), 7.37 (1H, t), 7.65(1H, s), 7.70 (1H, d), 8.48 (1H, s). $^m/_z$(CI): 450 (MH$^+$; 100%).

EXAMPLE 74

N-(1,2,3,4-Tetrahydroisoquinolin-5-yl)-5-iodo-2-methoxy-4-trifluoromethyldiazirinylbenzamide, Trifluoroacethate $^1$H NMR(250 MHz, MeOD-d$^4$)δ: 3.11 (2H,t), 3.59 (2H, t), 4.14 (3H, s),4.40 (2H, s), 7.18 (1H, d), 7.38 (1H, t), 7.55(1H, s), 7.69 (1 H, d), 8.42 (1H, s). $^m/_z$(CI): 517 (MH$^+$; 80%).

EXAMPLE 75

N-(7-Iodo-2-methyl-1,2,3,4-tetrahydroisoquinolin-5-yl)-5-benzoyl-2-methoxybenzamide $^1$H NMR (CDCl$_3$)δ: 2.41 (3H, s), 2.70 (4H, s), 3.50 (2H, s), 4.10 (3H, s), 7.12–7.23 (2H, m), 7.41–7.68 (3H, m), 7.74–7.85(2H, m), 8.12 (1H, dd), 8.55(1H, s), 8.72 (1H, d), 9.61 (1H, br s).

EXAMPLE 76

N-(7-Iodo-1,2,3,4-tetrahydroisoquinolin-5-yl)-5-benzoyl-2-methoxybenzamide, Trifluoroacethate $^1$H NMR (250 MHz, DMSO-d$^6$)δ: 2.92 (2H, br s), 3.46 (2H, br s), 4.08 (3H, s), 4.32 (2H, br s), 7.42 (1H, d), 7.54–7.76 (6H, m), 7.98 (1H, d), 8.10 (1H, s), 8.21 (1H, s), 9.26 (2H, br s), 9.98 (1H, s). $^m/_z$(CI, API-): 511 (M$^+$-H).

EXAMPLE 77

N-(5-Iodo-1,2,3,4-tetrahydroisoquinolin-7-yl)-5-benzoyl-2-methoxybenzamide, Trifluoroacethate $^1$H NMR (250 MHz, DMSO-d$^6$)δ: 2.82 (2H, t), 3.44 (2H, br s), 4.01 (3H, s), 4.31 (2H, br s), 7.38 (1H, d), 7.57–7.72 (6H, m), 7.95–8.00 (2H, m), 8.22 (1H, s), 9.15(2H, br s), 10.35(1H, s). $^m/_z$(CI): 513 (MH$^+$; 100%).

EXAMPLE 78

N-(5-Iodo-1,2,3,4-tetrahydroisoquinolin-7-yl)-2-methoxy-4-trifluoromethyldiazirinylbenzamide, Trifluoroacethate $^1$H NMR (250 MHz, DMSO-d$^6$)δ: 2.82 (2H, br s), 3.50 (2H, br s), 3.93 (3H, s), 4.30 (2H, br s), 7.24 (1H, d), 7.34 (1H, d), 7.41–7.48 (1H, m), 7.64–7.78 (2H, m), 8.22 (1H, s), 9.20 (2H, br s), 10.25(1H, s). $^m/_z$(CI): 517 (MH$^+$; 100%).

EXAMPLE 79

N-(5-Iodo-1,2,3,4-tetrahydroisoquinolin-7-yl)-2-methoxy-5-trifluoromethyldiazirinylbenzamide, Trifluoroacethate $^1$H NMR (250 MHz, DMSO-d$^6$)δ: 2.82 (2H, br s), 3.43 (2H, br s), 3.91 (3H, s), 4.30 (2H, br s), 6.86 (1H, s), 7.12 (1H, d), 7.68–7.71 (2H, m), 8.20 (1H, s), 9.18 (2H, br s), 10.33 (1H, s).

EXAMPLE 80

N-(2-Methyl-1,2,3,4-tetrahydroisoquinolin-5-yl)-2-methoxy-5-trifluoroacetyl Benzamide $^1$H NMR (DMSO-d$^6$)δ: 2.54 (3H, s), 2.82 (4H, s), 3.73 (2H, s), 4.29 (3H, s), 6.91 (1H, d), 7.18 (1H, t), 7.31 (1H, d), 8.04 (1H, d), 8.41 (1H, d), 8.96 (1H, s), 9.61 (1H, br s). $^m/_z$(CI): 393 (MH$^+$)

EXAMPLE 81

N-(2-Methyl-1,2,3,4-tetrahydroisoquinolin-5-yl)-2-methoxy-4-trifluoromethyldiazirinyl Benzamide $^1$H NMR (DMSO-d$^6$)δ: 2.52 (3H, s), 2.83 (4H, s), 3.69 (2H, s), 4.09 (3H, s), 6.78 (1H, s), 6.86 (1H, d), 6.97 (1H, d), 7.21(1H, t), 8.08 (1H, d), 8.37 (1H, d), 9.56 (1H, br s).

EXAMPLE 82

N-(1,2,3,4-Tetrahydroisoquinolin-7-yl)-5-iodo-2-methoxy-4-trifluoromethyldiazirinylbenzamide, Trifluoroacethate $^m/_z$(CI): 517 (MH$^+$; 100%).

EXAMPLE 83

N-(1,2,3,4-Tetrahydroisoquinolin-5-yl)-5-(4-iodobenzoyl)-2-methoxybenzamide, Trifluoroacethate $^1$H NMR (250 MHz, DMSO-d$^6$)δ: 2.98 (2H, t), 3.42 (2H, br s), 4.08 (3H, s), 4.35(2H, br s), 7.12 (1H, d), 7.33(1H, t), 7.41 (1H, d), 7.52 (2H, d), 7.65(1H, d), 7.95–8.03 (3H, m), 8.16 (1H, d), 9.09 (2H, br s), 9.90 (1H, s).

EXAMPLE 84

N-(7-Iodo-1,2,3,4-tetrahydroisoquinolin-5-yl)-2-methoxy-5-trifluoromethydiazirinyl Benzamide, Trifluoroacethate $^1$H NMR (250 MHz, DMSO-d$^6$)δ: 2.90 (2H, br s), 3.45 (2H, br s), 4.01 (3H, s), 4.32 (2H, br s), 7.38 (1H, d), 7.50–7.54 (2H, m), 7.70 (1H, s), 8.11 (1H, s), 9.28 (2H, br s), 9.91 (1H, s). $^m/_z$(CI): 517 (MH$^+$; 100%).

EXAMPLE 85

N-(2-Methyl-1,2,3,4-tetrahydroisoquinolin-7-yl)-4-chloro-2-methoxybenzamide $^1$H NMR (CDCl$_3$)δ: 2.47 (3H, s), 2.70 (2H, t), 2.90 (2H, t), 3.61 (2H, s), 4.06 (3H, s), 7.03 (1H, s), 7.11 (1H, t), 7.47 (1H, s), 8.22 (1H, d, J=7 Hz), 9.55(1H, br s). $^m/_z$(API$^+$): MH$^+$at 333 (37%) and 331 (100%)

EXAMPLE 86

N-(2-Methyl-1,2,3,4-tetrahydroisoquinolin-7-yl)-2-methoxy-4-methylthiobenzamide $^1$H NMR (CDCl$_3$) δ: 2.53 (3H, s); 2.54 (3H, s), 2.69 (2H, t), 2.88 (2H, t), 3.60 (2H, s), 4.05(3H, s), 6.86 (1H, d), 6.95(1H, dd), 7.08 (1H, d, J=7 Hz), 7.28 (1H, dd), 7.49 (1H, d), 8.22 (1H, d, J=7 Hz), 9.64 (1H, br s). $^m/_z$(API$^+$): 343 (MH$^+$; 100%).

EXAMPLE 87

N-(8-Fluoro-2-methyl-1,2,3,4-tetrahydroisoquinolin-5-yl)-4-t-butyl-2-methoxybenzamide $^m/_z$(API$^+$): 371 (MH$^+$; 80%).

EXAMPLE 88

N-(2-Methyl-1,2,3,4-tetrahydroisoquinolin-5-yl)-5-iso-butyroyl-4-iso-propoxy-2-methoxybenzamide $^1$H NMR (CDCl$_3$) δ: 1.15(6H, d, J=6.6 Hz), 1.51 (6H, d, J=6 Hz), 2.48 (3H, s), 2.73 (2H, t), 2.84 (2H, t), 3.46 (1H, m), 3.61 (2H, s), 3.94 (3H, s), 4.90 (1H, m), 6.54 (1H, s), 6.88 (1H, d, J=7 Hz), 7.20 (1H, t, J=7 Hz), 7.90 (1H, d, J=7 Hz), 8.58 (1H, s), 9.29 (1H, br s).

PHARMACOGICAL DATA

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It as been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Watman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resulthant curve is used to provide an estimate of compound affinity in terms of pKi value.

Results

Compounds of this invention were active in this test. For example, compounds of Examples 1, 7, 10, 13, 16, 17, 19, 20, 23, 25, 35, 37, 45, 46, 49, 50, 52, 68, 70 and 71 gave pKi values greater than 7.

2. MEST Test

The maximal electroshock seizure threshold (MEST) test in rodents is particularly sensitive for detecting potential anticonvulsant properties[1]. In this model, anticonvulsant agents elevate the threshold to electrically-induced seizures whilst proconvulsants lower the seizure threshold.

Method

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and sthandard error required to induce a tonic seizure in 50% ($CC_{50}$) of the mice in a particular treatment group is determined by the 'up and down' method of Dixon and Mood (1948)[2]. Sthatistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Consthant Current Shock Generator with totally variable control of shock level from 0 to 300 mA and steps of 2 mA are usually used.

Drugs are suspended or dissolved in 1% methyl cellulose.

References

1. Loscher, W. and Schmidt, D. (1988). Epilepsy Res., 2, 145–181

2. Dixon, W. J. and Mood, A. M. (1948). J. Amer. Sthat. Assn., 43, 109–126

3. Litchfield, J. T. and Wilcoxon, F.(1949). J. Pharmacol. exp. Ther., 96, 99–113

Results

Compounds of this invention dosed by the oral route as a suspension in methyl cellulose and tested one hour post dosing showed an increase in seizure threshold. All compounds tested showed significant % increase at 30 mg/kg po. Preferred compounds are hereinafter mentioned.

What is claimed is:

1. A compound of formula (I) or pharmaceutically acceptable salt thereof:

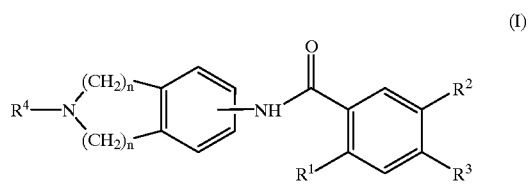

where n and p are independently integers from 1 to 4 and (n+p) is from 2 to 5;

$R^1$ is $C_{1-6}$alkylO-;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO-, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-, $C_{1-6}$alkylS-, $C_{1-6}$alkylSO$_2$—, $(C_{1-4}$alkyl$)_2$NSO$_2$— or $(C_{1-4}$alkyl)NHSO$_2$—;

$R^3$ is hydrogen, halogen, $NO_2$, CN, $N_3$, trifluoromethyldiazirinyl, $C_{1-6}$alkylO-, $C_{1-6}$ alkylS-, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-, or —NR$^5$R$^6$ were R$^5$ is hydrogen or $C_{1-4}$ alkyl, and $R^6$ is hydrogen, $C_{1-4}$alkyl, —CHO, —CO$_2$C$_{1-4}$alkyl or —COC$_{1-4}$alkyl; $R^4$ is hydrogen, $C_{1-6}$ alkyl, $C_{1-6}$ alkenyl, or $C_{1-6}$ alkynyl; but excluding the compound 2,4,5-trimethoxy-N-(2-methyl-1,2,3,4-tetrahydroisoquinolin-5-yl)benzamide.

2. A compound according to claim 1 in which $R^1$ is methoxy, ethoxy or n-propoxy.

3. A compound according to claim 1 in which $R^2$ is hydrogen, methoxy, bromo, chloro, iodo, acetyl, pivaloyl, iso-butyroyl, benzoyl, trifluoromethyl, trifluoroacetyl, n-propylsulfonyl, isopropylsulfonyl or dimethylsulfamoyl.

4. A compound according to claim 1 in which $R^3$ is hydrogen, methyl, ethyl, n-butyl, phenyl, methoxy, ethoxy, iso-propyl, t-butyl, phenyl, methoxy, ethoxy, iso-propoxy, n-butoxy, phenoxy, benzyloxy, amino, acetylamino, nitro, benzoyl, iodobenzoyl, chloro or azido.

5. A compound according to claim 1 in which $R^4$ is hydrogen, methyl, ethyl or propyl.

6. A compound as defined in claim 1 where $R^2$ or $R^3$ are independently $N_3$, benzoyl, or trifluoromethyl-diazerinyl, and all other variables are as defined in claim 1.

7. N-(2-methyl-1,2,3,4-tetrahydroisoquinolin-5-yl)-4-amino-5-chloro-2-methoxybenzamide N-(2-methyl-1,2,3,4-tetrahydroisoquinolin-5-yl)-2,4-dimethoxybenzamide N-(2-methyl-1,2,3,4-tetrahydroisoquinolin-5-yl)-2-methoxybenzamide N-(2-methyl-1,2,3,4-tetrahydroisoquinolin-5-yl)-5-chloro-2-methoxybenzamide N-(2-methyl-1,2,3,4-tetrahydroisoquinolin-5-yl)-4-chloro-2-methoxybenzamide N-(2-methyl-1,2,3,4-tetrahydroisoquinolin-5-yl)-4-acetylamino-5-bromo-2-methoxybenzamide N-(2-methyl-1,2,3,4-tetrahydroisoquinolin-5-yl)-4-amino-5-bromo-2-methoxybenzamide N-(2-methyl-1,2,3,4-tetrahydroisoquinolin-5-yl)-4-azido-5-iodo-2-methoxybenzamide N-(2-methyl-1,2,3,4-tetrahydroisoquinolin-5-yl)-4-acetylamino-5-chloro-2-propoxybenzamide N-(2-methyl-1,2,3,4-tetrahydroisoquinolin-5-yl)-4-amino-5-chloro-2-propoxybenzamide
N-(2-methyl-1,2,3,4-tetrahydroisoquinolin-5-yl)-4-acetylamino-2-methoxybenzamide
N-(2-methyl-1,2,3,4-tetrahydroisoquinolin-5-yl)-5-chloro-2-methoxy-4-nitrobenzamide
N-(2-methyl-1,2,3,4-tetrahydroisoquinolin-5-yl)-4-amino-5-iodo-2-methoxybenzamide
N-(2-methyl-1,2,3,4-tetrahydroisoquinolin-5-yl)-4-benzyloxy-5-chloro-2-methoxybenzamide
N-(2-methyl-1,2,3,4-tetrahydroisoquinolin-5-yl)-4,5-dichloro-2-methoxybenzamide
N-(2-methyl-1,2,3,4-tetrahydroisoquinolin-5-yl)-5-chloro-2,4-dimethoxybenzamide
N-(2-methyl-1,2,3,4-tetrahydroisoquinolin-5-yl)-5-bromo-2,4-dimethoxybenzamide
N-(2-methyl-1,2,3,4-tetrahydroisoquinolin-5-yl)-5-[3-(trifluoromethyl)-3H-diazirin-3-yl]-2-methoxybenzamide
N-(1,2,3,4-tetrahydroisoquinolin-5-yl)-5-chloro-2,4-dimethoxybenzamide
N-(2-methyl-1,2,3,4-tetrahydroisoquinolin-5-yl)-5-chloro-2-methoxy-4-methylbenzamide
N-(2-n-propyl-1,2,3,4-tetrahydroisoquinolin-5-yl)-5-chloro-2,4-dimethoxybenzamide
N-(2-ethyl-1,2,3,4-tetrahydroisoquinolin-5-yl)-5-chloro-2,4-dimethoxybenzamide
N-(2-methyl-1,2,3,4-tetrahydroisoquinolin-5-yl)-5-chloro-4-ethoxy-2-methoxybenzamide
N-(2-methyl-1,2,3,4-tetrahydroisoquinolin-5-yl)-2,5-dimethoxybenzamide
N-(2-methyl-1,2,3,4-tetrahydroisoquinolin-5-yl)-5-bromo-2-methoxy-4-methylbenzamide
N-(2-methyl-1,2,3,4-tetrahydroisoquinolin-5-yl)-5-dimethylsulfamoyl-2-methoxybenzamide
N-(2-methyl-1,2,3,4-tetrahydroisoquinolin-5-yl)-4-benzoyl-2-methoxybenzamide
N-(2-methyl-1,2,3,4-tetrahydroisoquinolin-5-yl)-5-benzoyl-2-methoxybenzamide
N-(2-methyl-1,2,3,4-tetrahydroisoquinolin-8-yl)-4-acetylamino-5-chloro-2-methoxybenzamide
N-(2-methyl-1,2,3,4-tetrahydroisoquinolin-8-yl)-4-amino-5-chloro-2-methoxybenzamide
N-(2,3-dihydro-2-methyl-1H-isoindol-4-yl)-5-chloro-2,4-dimethoxybenzamide.
N-(3-methyl-2,3,4,5-tetrahydro-1H-3-benzazepine-6-yl)-4-tert-butyl-2-methoxy-benzamide
N-(1,2,3,4-tetrahydroisoquinolin-6-yl)-4-tert-butyl-2-methoxybenzamide
N-(2-methyl-1,2,3,4-tetrahydroisoquinolin-6-yl)-4-tert-butyl-2-methoxybenzamide
N-(2-methyl-1,2,3,4-tetrahydroisoquinolin-5-yl)-4-tert-butyl-2-methoxybenzamide
N-(2-methyl-1,2,3,4-tetrahydroisoquinolin-5-yl)-4-n-butyl-2-methoxy-5-chloro-benzamide
N-(2-methyl-1,2,3,4-tetrahydroisoquinolin-5-yl)-4-ethyl-2-methoxy-5-chloro benzamide
N-(2-methyl-1,2,3,4-tetrahydroisoquinolin-5-yl)-4-tert-butyl-2-methoxy-5-chloro-benzamide
N-(2-methyl-1,2,3,4-tetrahydroisoquinolin-5-yl)-2-methoxy-4-phenylbenzamide
N-(1,2,3,4-tetrahydroisoquinolin-5-yl)-4-tert-butyl-2-methoxybenzamide
N-(2-methyl-1,2,3,4-tetrahydroisoquinolin-5-yl)-4-iso-propyl-2-methoxybenzamide
N-(2-methyl-1,2,3,4-tetrahydroisoquinolin-5-yl)-5-chloro-4-iso-propyl-2-methoxy-benzamide
N-(1,2,3,4-tetrahydroisoquinolin-5-yl)-5-chloro-4-tert-butyl-2-methoxybenzamide
N-(2-methyl-1,2,3,4-tetrahydroisoquinolin-5-yl)-4-ethyl-2-methoxybenzamide
N-(2-methyl-1,2,3,4-tetrahydroisoquinolin-5-yl)-5-bromo-4-iso-propoxy-2-methoxy-benzamide
N-(2-methyl-1,2,3,4-tetrahydroisoquinolin-5-yl)-4-iso-propyl-5-trifluoromethyl-2-methoxybenzamide
N-(2-methyl-1,2,3,4-tetrahydroisoquinolin-5-yl)-4-iso-propoxy-2-methoxy-5-trifluoromethyl-benzamide
N-(2-methyl-1,2,3,4-tetrahydroisoquinolin-5-yl)-5-bromo-4-iso-propyl-2-methoxybenzamide
N-(2-methyl-1,2,3,4-tetrahydroisoquinolin-5-yl)-5-iso-butyroyl-2-methoxy-benzamide
N-(2-methyl-1,2,3,4-tetrahydroisoquinolin-5-yl)-5-pivaloyl-2-methoxybenzamide
N-(2-methyl-1,2,3,4-tetrahydroisoquinolin-7-yl)-5-chloro-2-methoxy-4-iso-propoxybenzamnide
N-(2-methyl-1,2,3,4-tetrahydroisoquinolin-7-yl)-5-bromo-2,4-dimethoxybenzamide
N-(2-methyl-1,2,3,4-tetrahydroisoquinolin-7-yl)-4-tert-butyl-2-methoxybenzamide
N-(2-methyl-1,2,3,4-tetrahydroisoquinolin-7-yl)-2-methoxy-4-methyl-5-trifluoromethylbenzamide
N-(2-methyl-1,2,3,4-tetrahydroisoquinolin-7-yl)-2-methoxybenzamide
N-(2-methyl-1,2,3,4-tetrahydroisoquinolin-7-yl)-2,4-dimethoxybenzamide
N-(2-methyl-1,2,3,4-tetrahydroisoquinolin-7-yl)-5-chloro-2-methoxybenzamide
N-(2-methyl-1,2,3,4-tetrahydroisoquinolin-5-yl)-4-iso-propoxy-2-methoxybenzamide
N-(2-methyl-1,2,3,4-tetrahydroisoquinolin-5-yl)-5-dimethylsulfamoyl-2,4-dimethoxybenzamide
N-(2-methyl-1,2,3,4-tetrahydroisoquinolin-5-yl)-2-methoxy-5-iso-propylsulfonylbenzamide
N-(2-methyl-1,2,3,4-tetrahydroisoquinolin-5-yl)-5-chloro-2-methoxy-4-phenylbenzamide
N-(1,2,3,4-Tetrahydroisoquinolin-5-yl)-5-bromo-2,4-dimethoxybenzamide
N-(2-methyl-1,2,3,4-tetrahydroisoquinolin-5-yl)-2-methoxy-5-n-propylsulfonylbenzamide
N-(2-methyl-1,2,3,4-tetrahydroisoquinolin-5-yl)-2,4-dimethoxy-5-trifluoromethylbenzamide
N-(2-methyl-1,2,3,4-tetrahydroisoquinolin-5-yl)-2-methoxy-4-methyl-5-trifluoromethylbenzamide
N-(2-methyl-1,2,3,4-tetrahydroisoquinolin-5-yl)-4-acetyl-2,4-dimethoxybenzamide
N-(2-methyl-1,2,3,4-tetrahydroisoquinolin-5-yl)-5-bromo-4-ethyl-2-methoxybenzamide
N-(2-methyl-1,2,3,4-tetrahydroisoquinolin-5-yl)-4-ethyl-2-methoxy-5-trifluoromethylbenzamide
N-(2-methyl-1,2,3,4-tetrahydroisoquinolin-5-yl)-4-n-butoxy-5-chloro-2-methoxybenzamide
N-(2-methyl-1,2,3,4-tetrahydroisoquinolin-5-yl)-2-methoxy-4-iso-propyloxy-5-acetyl-benzamide
N-(2-methyl-1,2,3,4-tetrahydroisoquinolin-5-yl)-5-chloro-2-methoxy-4-iso-propoxybenzamide
N-(2-methyl-1,2,3,4-tetrahydroisoquinolin-5-yl)-2-methoxy-5-iodo-4-trifluoromethyldiazirinyl benzamide
N-(1,2,3,4-tetrahydroisoquinolin-5-yl)-4-azido-5-iodo-2-methoxybenzamide
N-(1,2,3,4-tetrahydroisoquinolin-5-yl)-5-iodo-2-methoxy-4-trifluoromethyldiazirinylbenzamide
N-(7-iodo-2-methyl-1,2,3,4-tetrahydroisoquinolin-5-yl)-5-benzoyl-2-methoxybenzamide
N-(7-iodo-1,2,3,4-tetrahydroisoquinolin-5-yl)-5-benzoyl-2-methoxybenzamide N-(5-iodo-1,2,3,4-tetrahydroisoquinolin-7-yl)-5-benzoyl-2-methoxybenzamide N-(5-iodo-1,2,3,4-tetrahydroisoquinolin-7-yl)-2-methoxy-4-trifluoromethyldiazirinylbenzamide N-(5-iodo-1,2,3,4-tetrahydroisoquinolin-7-yl)-2-methoxy-5-trifluoromethyldiazirinylbenzamide N-(2-methyl-1,2,3,4-tetrahydroisoquinolin-5-yl)-2-methoxy-5-trifluoroacetyl benzamide N-(2-methyl-1,2,3,4-tetrahydroisoquinolin-5-yl)-2-methoxy-5-trifluoroacetyl benzamide N-(2-methyl-1,2,3,4-tetrahydroisoquinolin-5-yl)-2-methoxy-4-trifluoromethyldiazirinylbenzamide N-(1,2,3,4-tetrahydroisoquinolin-7-yl)-5-iodo-2-methoxy-4-trifluoromethyldiazirinylbenzamide N-(1,2,3,4-tetrahydroisoquinolin-5-yl)-5-(4-iodobenzoyl)-2-methoxybenzamide N-(7-iodo-1,2,3,4-tetrahydroisoquinolin-5-yl)-2-methoxy-5-trifluoromethyldiazirinylbenzamide;

N-(2-Methyl-1,2,3,4-tetrahydroisoquinolin-7-yl)-4-chloro-2-methoxybenzamide

N-(2-Methyl-1,2,3,4-tetrahydroisoquinolin-7-yl)-2-methoxy-4-methylthiobenzamide

N-(8-Fluoro-2-methyl-1,2,3,4-tetrahydroisoquinolin-5-yl)-4-t-butyl-2-methoxybenzamide N-(2-Methyl-1,2,3,4-tetrahydroisoquinolin-5-yl)-5-iso-butyroyl-4-iso-propoxy-2-methoxybenzamide, and N-(2-methyl-1,2,3,4-tetrahydroisoquinolin-5-yl)-4-n-butoxy-2-methoxybenzamide.

8. A pharmaceutical composition for use in the treatment and/or prevention of anxiety, mania, depression, panic disorders and/or aggression, disorders associated with a subarachnoid haemorrhage or neural shock, the effects associated with withdrawal from substhances of abuse, disorders treatable and/or preventable with anti-convulsive agents, Parkinson's disease, phychosis, migraine, cerebral ischaemia, Alzheimer's disease and other degenerative diseases, schizophrenia, obsessive compulsive disorders (OCD), neurological deficits associated with AIDS, sleep disorders, tics, traumatic brain injury, tinnitus, neuralgia, trigeminal neuralgia, neuropathic pain, dental pain, cancer pain, inappropriate neuronal activity resulting in neurodysthesias in diseases, ataxias, muscular rigidity (spacicity), temporomandibular joint dysfunction, and amyptrophic lateral sclerosis (ALS) which comprises a compound of formula (I) as defined in claim 1, without excluding 2,4,5-trimethoxy-N-(2-methyl-1,2,3,4-tetrahydroisoquinolin-5-yl)benzamide, or a pharmaceutically acceptable salt or solvate thereof, and a pharmaceutically acceptable carrier.

9. A method of treatment and/or prevention of anxiety, mania, depression, panic disorders and/or aggression, disorders associated with a subarachnoid haemorrhage or neural shock, the effects associated with withdrawal from substhances of abuse, disorders treatable and/or preventable with anti-convulsive agents, Parkinson's disease, phychosis, migraine, cerebral ischaemia, Alzheimer's disease and other degenerative diseases, schizophrenia, obsessive compulsive disorders (OCD), neurological deficits associated with AIDS, sleep disorders, tics, traumatic brain injury, tinnitus, neuralgia, trigeminal neuralgia, neuropathic pain, dental pain, cancer pain, inappropriate neuronal activity resulting in neurodysthesias in diseases, ataxias, muscular rigidity (spacicity), temporomandibular joint dysfunction, and amyptrophic lateral sclerosis (ALS) comprising administering to the sufferer in need thereof an effective or preventive amount of a compound of formula (I) as defined in claim 1, without excluding 2,4,5-trimethoxy-N-(2-methyl-1,2,3,4-tetrahydroisoquinolin-5-yl)benzamide, or a pharmaceutically acceptable salt or solvate thereof.

10. A process for the preparation of a compound of formula (I), which comprises reacting a compound of formula (II)

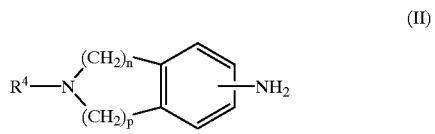

(II)

where n and p are independently integers from 1 to 4 and (n+p) is from 2 to 5; and $R^{4A}$ is $R^4$ wherein $R^4$ is hydrogen, $C_{1-6}$alky, $C_{1-6}$alkenyl, or $C_{1-6}$alkynyl, or a group convertible to $R^4$ with a compound of formula (III)

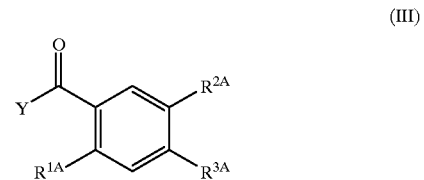

(III)

where Y is Cl or OH, and $R^{1A}$, $R^{2A}$ and $R^{3A}$ are respectively $R^1$, $R^2$ and $R^3$ wherein:

$R^1$ is $C_{1-6}$alkylO, $R^2$ is hydrogen, halogen, CN, $N_3$, trifluoromethyldiazirinyl, $CF_3$, $CF_3O—$, $CF_3S—$, $CF_3CO—$, $C_{1-6}$alkyl, $C_{3-6}$cycloalkyl, $C_{3-6}$cycloalky-$C_{1-4}$alkyl-, $C_{1-6}$alkylO, $C_{1-6}$-alkylCO-, $C_{3-6}$cycloalkylCO-, $C_{3-6}$ cycloalkyl-$C_{1-4}$alkylCO-; phenyl, phenoxy, benzyloxy, benzoyl, phenol-$C_{1-4}$alkyl-, $C_{1-6}$ alkylS-, $C_{1-6}$alkylSO$_2$—, $(C_{1-4}$alkyl$)_2$NSO$_2$— or $(C_{1-4}$alkyl)NHSO$_2$—;

$R^3$ is hydrogen, halogen, $NO_2$, CN, $N_3$, trifluoromethyldiazirinyl, $C_{1-6}$alkylO-, $C_{1-6}$alkylS-, $C_{1-6}$alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO—$, $C_{1-6}$alkylCO-, $C_{3-6}$cycloalkylCO-, $C_{3-6}$-cycloalkyl-$C_{1-4}$alkylCO-, phenyl, phenoxy, benzyloxy, benzoyl, phenyl-$C_{1-4}$alkyl-, or $—NR_5R_6$ where $R_5$is hydrogen or $C_{1-4}$alkyl, and $R_6$ is hydrogen, $C_{1-4}$alkyl, $—CHO$, $—CO_2C_{1-4}$alkyl or $—COC_{1-4}$alkyl;

or groups convertible to $R^1$, $R^2$ and $R^3$;

and where required converting a $R^{1A}$, $R^{2A}$, $R^{3A}$ or $R^{4A}$ group to a $R^1$, $R^2$, $R^3$ or $R^4$ group, converting one $R^1$, $R^2$, $R^3$ or $R^4$ group to another $R^1$, $R^2$, $R^3$ or $R^4$ group, converting a hydrochloride salt to the free base or another pharmaceutically acceptable salt or converting the free base to a pharmaceutically acceptable salt.

11. A pharmaceutical composition according to claim 8 wherein the substhances of abuse is chosen from the group comprising cocaine, nicotine, alcohol and benzodiazepines.

12. A pharmaceutical composition according to claim 8 wherein the disorder treatable and/or preventable with anti-convulsive agents is chosen from the group comprising epilepsy and post-traumatic epilepsy.

13. A pharmaceutical composition according to claim 8 wherein the sleep disorder is chosen from the group comprising circadian rhythm disorders, insomnia and narcolepsy.

14. A pharmaceutical composition according to claim 8 wherein the disease causing inappropriate neuronal activity resulting in neurodysthesias is chosen from the group comprising diabetes, MS and motor neuron disease.

15. A pharmaceutical composition according to claim 8 wherein the tic is Giles de la Tourette's syndrome.

16. A method of treatment according to claim 9 wherein the substhances of abuse is chosen from the group comprising cocaine, nicotine, alcohol and benzodiazepines.

17. A method of treatment according to claim 9 wherein the disorder treatable and/or preventable with anti-convulsive agents is chosen from the group comprising epilepsy and post-traumatic epilepsy.

18. A method of treatment according to claim 9 wherein the sleep disorder is chosen from the group comprising circadian rhythm disorders, insomnia and narcolepsy.

19. A method of treatment according to claim 9 wherein the disease causing inappropriate neuronal activity resulting in neurodysthesias is chosen from the group comprising diabetes, MS and motor neuron disease.

20. A method of treatment according to claim 9 wherein the tic is Giles de la Tourette's syndrome.

\* \* \* \* \*